(12) United States Patent
Burnham et al.

(10) Patent No.: US 12,178,552 B1
(45) Date of Patent: Dec. 31, 2024

(54) SYSTEMS AND PROCESSES FOR DETECTING OXYGEN SATURATION AND COMPENSATING FOR SKIN TONE VARIATION

(71) Applicant: Huxley Medical, Inc., Atlanta, GA (US)

(72) Inventors: Daniel Burnham, Atlanta, GA (US); Behnam Molavi, Redmond, WA (US); Mohsen Safaei Mohammadabadi, Smyrna, GA (US); Pannaga Sameer Kaushik Gummuluru, Kennedale, TX (US); Matias Teixeira Prates, Kennesaw, GA (US)

(73) Assignee: Huxley Medical, Inc., Atlanta, GA (US)

( * ) Notice: Subject to any disclaimer, the term of this patent is extended or adjusted under 35 U.S.C. 154(b) by 0 days.

(21) Appl. No.: 18/636,180

(22) Filed: Apr. 15, 2024

Related U.S. Application Data

(63) Continuation-in-part of application No. 18/402,925, filed on Jan. 3, 2024, which is a continuation-in-part
(Continued)

(51) Int. Cl.
*A61B 5/02* (2006.01)
*A61B 5/1455* (2006.01)
*A61B 5/318* (2021.01)

(52) U.S. Cl.
CPC .............. *A61B 5/02* (2013.01); *A61B 5/1455* (2013.01); *A61B 5/318* (2021.01)

(58) Field of Classification Search
CPC .......... A61B 5/02; A61B 5/1455; A61B 5/318
See application file for complete search history.

(56) References Cited

U.S. PATENT DOCUMENTS

| 1,248,586 A | 12/1917 | Wood |
| 3,052,232 A | 9/1962 | Zworykin |
(Continued)

FOREIGN PATENT DOCUMENTS

| AU | 2015253309 | 11/2015 |
| CN | 218978894 U * | 5/2023 |
(Continued)

OTHER PUBLICATIONS

Renesas, OB1203 Pulse Oximeter Algorithm for SpO2, Heart Rate, and Respiration Rate; Published Apr. 25, 2022, https://www.renesas.com/us/en/document/apn/ob1203-pulse-oximeter-algorithm-spo2-heart-rate-and-respiration-rate (Year: 2022).*
(Continued)

*Primary Examiner* — Jonathan T Kuo
(74) *Attorney, Agent, or Firm* — Husch Blackwell LLP; Bryan D. Stewart; Paige E. Reese

(57) ABSTRACT

The present disclosure relates to systems and processes for optimizing the detection of a patient's heartbeats, which may be useful in detection of the patient's oxygen saturation, as well as systems and processes for improving and optimizing the PPG signal quality of those patients with highly pigmented skin. In various embodiments, the process may comprise the steps of: receiving, from a radio, red data, infrared (IR) data, and a series of heartbeats associated with a time period; computing a series of peaks of the red data and IR data for the time period; computing a subset of the red data and IR data; estimating an oxygen saturation percentage (SpO2%) for the patient by computing an optical ratio of the red data and IR data included in the subset; and displaying on a computer screen the estimated SpO2% for the patient.

23 Claims, 24 Drawing Sheets

Related U.S. Application Data of application No. 18/299,539, filed on Apr. 12, 2023, now Pat. No. 12,076,117, which is a continuation of application No. 17/833,894, filed on Jun. 6, 2022, now Pat. No. 11,660,005.

(60) Provisional application No. 63/496,264, filed on Apr. 14, 2023, provisional application No. 63/478,494, filed on Jan. 4, 2023, provisional application No. 63/196,778, filed on Jun. 4, 2021.

(56) References Cited

U.S. PATENT DOCUMENTS

| | | |
|---|---|---|
| 3,195,535 A | 7/1965 | Westermann |
| 3,638,642 A | 2/1972 | Heflin |
| 4,104,728 A | 8/1978 | Kasubuchi |
| 4,121,573 A | 10/1978 | Crovella |
| 4,957,109 A | 9/1990 | Groeger |
| 5,050,613 A | 9/1991 | Newman |
| 5,251,286 A | 10/1993 | Weiner |
| 5,307,818 A | 5/1994 | Segalowitz |
| 5,546,811 A | 8/1996 | Rogers |
| 5,633,711 A | 5/1997 | Nelson |
| 5,672,830 A | 9/1997 | Rogers |
| 5,734,470 A | 3/1998 | Rogers |
| 5,800,478 A | 9/1998 | Chen |
| 5,812,261 A | 9/1998 | Nelson |
| 5,951,881 A | 9/1999 | Rogers |
| 5,982,482 A | 11/1999 | Nelson |
| 6,016,202 A | 1/2000 | Fuchs |
| 6,033,202 A | 3/2000 | Bao |
| 6,052,185 A | 4/2000 | Banet |
| 6,069,703 A | 5/2000 | Banet |
| 6,148,127 A | 11/2000 | Adams |
| 6,150,668 A | 11/2000 | Bao |
| 6,169,831 B1 | 1/2001 | Adams |
| 6,181,852 B1 | 1/2001 | Adams |
| 6,192,177 B1 | 2/2001 | Admunson |
| 6,252,253 B1 | 6/2001 | Bao |
| 6,256,100 B1 | 7/2001 | Banet |
| 6,275,629 B1 | 8/2001 | Eggleton |
| 6,285,812 B1 | 9/2001 | Admunson |
| 6,303,182 B1 | 10/2001 | Eggleton |
| 6,307,988 B1 | 10/2001 | Eggleton |
| 6,329,226 B1 | 12/2001 | Jones |
| 6,337,761 B1 | 1/2002 | Rogers |
| 6,351,585 B1 | 2/2002 | Amundson |
| 6,363,096 B1 | 3/2002 | Dodabalapur |
| 6,370,300 B1 | 4/2002 | Eggleton |
| 6,410,416 B1 | 6/2002 | Dodabalapur |
| 6,427,040 B1 | 7/2002 | Ahuja |
| 6,438,277 B1 | 8/2002 | Eggleton |
| 6,529,676 B2 | 3/2003 | Eggleton |
| 6,589,629 B1 | 7/2003 | Bao |
| 6,655,286 B2 | 12/2003 | Rogers |
| 6,719,868 B1 | 4/2004 | Schueller |
| 6,736,985 B1 | 5/2004 | Bao |
| 6,743,982 B2 | 6/2004 | Biegesen |
| 6,753,131 B1 | 6/2004 | Rogers |
| 6,769,769 B2 | 8/2004 | Podoleanu |
| 6,778,734 B2 | 8/2004 | Baldwin |
| 6,795,198 B1 | 9/2004 | Fuchs |
| 6,829,415 B2 | 12/2004 | Kroupenkine |
| 6,856,731 B2 | 2/2005 | Rogers |
| 6,895,688 B2 | 5/2005 | Acharya |
| 6,927,860 B2 | 8/2005 | Podoleanu |
| 6,946,332 B2 | 9/2005 | Loo |
| 7,110,646 B2 | 9/2006 | Eggleton |
| 7,139,478 B2 | 11/2006 | Eggleton |
| 7,195,733 B2 | 3/2007 | Rogers |
| 7,229,847 B2 | 6/2007 | Hsu |
| 7,330,273 B2 | 2/2008 | Podoleanu |
| 7,417,741 B2 | 8/2008 | Podoleanu |
| 7,439,096 B2 | 10/2008 | Baldwin |
| 7,521,292 B2 | 4/2009 | Rogers |
| 7,557,367 B2 | 7/2009 | Rogers |
| 7,704,684 B2 | 4/2010 | Rogers |
| 7,705,280 B2 | 4/2010 | Nuzzo |
| 7,799,699 B2 | 9/2010 | Nuzzo |
| 7,943,491 B2 | 5/2011 | Nuzzo |
| 8,372,726 B2 | 2/2013 | De Graff |
| 8,734,339 B2 | 5/2014 | Rao |
| 9,061,494 B2 | 6/2015 | Rogers |
| 9,119,533 B2 | 9/2015 | Ghaffari |
| 9,247,637 B2 | 1/2016 | Hsu |
| 9,372,123 B2 | 6/2016 | Li |
| 9,545,285 B2 | 1/2017 | Ghaffari |
| 9,554,850 B2 | 1/2017 | Lee |
| 9,579,040 B2 | 2/2017 | Rafferty |
| 9,613,911 B2 | 4/2017 | Rogers |
| 9,622,680 B2 | 4/2017 | Ghaffari |
| 9,629,586 B2 | 4/2017 | Ghaffari |
| 9,702,839 B2 | 7/2017 | Ghaffari |
| 9,704,908 B2 | 7/2017 | De Graff |
| 9,706,647 B2 | 7/2017 | Hsu |
| 9,723,122 B2 | 8/2017 | Ghaffari |
| 9,723,711 B2 | 8/2017 | Elolampi |
| 9,750,421 B2 | 9/2017 | Ghaffari |
| 9,757,050 B2 | 9/2017 | Ghaffari |
| 9,810,623 B2 | 11/2017 | Ghaffari |
| 9,744,145 B1 | 12/2017 | Hsu |
| 9,746,829 B2 | 12/2017 | Fastert |
| 9,833,190 B2 | 12/2017 | Ghaffari |
| 9,894,757 B2 | 2/2018 | Arora |
| 9,899,330 B2 | 2/2018 | Dalal |
| 9,949,691 B2 | 4/2018 | Huppert |
| 10,024,743 B2 | 7/2018 | Davis |
| 10,032,709 B2 | 7/2018 | Rafferty |
| D825,537 S | 8/2018 | Li |
| 10,161,737 B2 | 12/2018 | Pegan |
| 10,186,546 B2 | 1/2019 | De Graff |
| 10,192,830 B2 | 1/2019 | Rogers |
| 10,244,949 B2 * | 4/2019 | Moyer .................. A61B 5/282 |
| 10,582,618 B2 | 3/2020 | Coleman |
| 10,898,084 B2 | 1/2021 | Khine |
| 11,207,002 B2 | 12/2021 | Khine |
| 2002/0180605 A1 | 12/2002 | Ozguz |
| 2005/0096513 A1 | 5/2005 | Ozguz |
| 2014/0275845 A1 | 9/2014 | Eagon |
| 2014/0275888 A1 | 9/2014 | Wegerich |
| 2015/0351689 A1 | 12/2015 | Adams |
| 2016/0302674 A1 * | 10/2016 | Moyer ............... A61B 5/02416 |
| 2016/0313176 A1 | 10/2016 | Lee |
| 2017/0079144 A1 | 3/2017 | Coleman |
| 2017/0156623 A1 | 6/2017 | Chu |
| 2017/0347894 A1 | 12/2017 | Bhushan |
| 2018/0177459 A1 | 6/2018 | Eletr et al. |
| 2019/0069788 A1 | 3/2019 | Coleman |
| 2019/0113326 A1 | 4/2019 | Pegan |
| 2019/0142625 A1 | 5/2019 | Goff |
| 2020/0069193 A1 | 3/2020 | Khine |
| 2020/0255791 A1 | 8/2020 | Yeo |
| 2021/0161405 A1 | 6/2021 | Khine |
| 2022/0009764 A1 | 1/2022 | Zhou |
| 2022/0280066 A1 | 9/2022 | Chu |

FOREIGN PATENT DOCUMENTS

| | | |
|---|---|---|
| EP | 3083248 | 8/2017 |
| EP | 3673797 | 7/2020 |
| EP | 3137038 | 12/2020 |
| EP | 3877830 | 8/2022 |
| WO | 2015095836 | 6/2015 |
| WO | 2015179320 | 11/2015 |
| WO | 2015179322 | 11/2015 |
| WO | 2017220526 | 12/2017 |
| WO | 2020092747 | 5/2020 |
| WO | 2020097505 | 5/2020 |
| WO | 2020228724 | 11/2020 |
| WO | 2021055496 | 3/2021 |
| WO | 2021142121 | 7/2021 |

(56) References Cited

OTHER PUBLICATIONS

Munck, et al., Multichannel seismocardiography: an imaging modality for investigating heart vibrations, Physiological Measurement, 2020, 12 pages, vol. 41.

Muthasamy, et al., An Overview of Respiratory Airflow Estimation Techniques: Acoustic vs Non-Acoustic, IEEE International Conference on Signal and Image Processing Applications, Sep. 2019, 5 pages.

Nara, et al., Novel Notch Detection Algorithm for Detection of Dicrotic Notch in PPG Signals, International Journal of Computer Applications, Jan. 2014, 5 pages, vol. 86 No. 17.

Nilsson, et al., Combined photoplethysmographic monitoring of respiration rate and pulse: a comparison between different measurement sites in spontaneously breathing subjects, Acta Anaesthesiol Scand, 2007, 8 pages, vol. 51.

Pandey, et al., Pulse Oximeter for Low SpO2 Level Detection Using Discrete Time Signal Processing Algorithm, Journal of Medical Devices, Jun. 2019, 8 pages, vol. 18.

Pandia, et al., Motion Artifact Cancellation to Obtain Heart Sounds From a Single Chest-Worn Accelerometer, IEEE ICASSP, 2010, 4 pages.

Pandia, et al., Extracting respiratory information from seismocardiogram signals acquired on the chest using a miniature accelerometer, Physiological Measurement, Sep. 2012, 19 pages, vol. 33.

Pandia, et al., A Frequency Domain Analysis of Respiratory Variations in the Seismocardiogram Signal, IEEE EMBS, Jul. 2013, 4 pages.

Racape, et al., Influence of sympathetic activation on myocardial contractility measured with ballistocardiography and seismocardiography during sustained end-expiratory apnea, Am J Physiol Regul Integr Comp Physiol, Sep. 2020, 10 pages.

Razjouyan, et al., Improving Sleep Quality Assessment Using Wearable Sensors by Including Information From Postural/Sleep Position Changes and Body Acceleration: A Comparison of Chest-Worn Sensors, Wrist Actigraphy, and Polysomnography, Journal of Clinical Sleep Medicine, 2017, 10 pages, vol. 13 No. 11.

Rusch, et al., Alternate Pulse Oximetry Algorithms for Sp02 Computation, University of South Florida, 1994, 2 pages.

Rusch, et al., Signal Processing Methods for Pulse Oximetry, Comput. Biol. Med., Oct. 1995, 17 pages, vol. 26 No. 2.

Morillo, et al., An Accelerometer-Based Device for Sleep Apnea Screening, IEEE Transactions on Information Technology in Biomedicine, Mar. 2010, 9 pages, vol. 10 No. 2.

Schlotthauer, et al., Measuring Complexity of Biomedical Signals, Hindawi Complexity, 2018, 4 pages, vol. 2018.

Shafiq, et al., Data Descriptor: Multimodal chest surface motion data for respiratory and cardiovascular monitoring applications, Scientific Data, Apr. 2017, 12 pages.

Skoric, et al., Relationship of the Respiration Waveform to a Chest Worn Inertial Sensor, IEEE, 2020, 4 pages.

Solà, et al., Chest Pulse-Wave Velocity: A Novel Approach to Assess Arterial Stiffness, IEEE Transactions on Biomedical Engineering, Jan. 2011, 9 pages, vol. 58 No. 1.

Sørensen, et al., Definition of Fiducial Points in the Normal Seismocardiogram, Scientific Reports, Oct. 2018, 11 pages.

Taebi, et al., Recent Advances in Seismocardiography, Vibration, 2019, 23 pages, vol. 2.

Tamura, Current progress of photoplethysmography and SPO2 for health monitoring, Biomedical Engineering Letters, Feb. 2019, 16 pages, vol. 9.

Tavakolian, Characterization and Analysis of Seismocardiogram for Estimation of Hemodynamic Parameters, Simon Fraser University, Fall 2010, 217 pages.

Telfer, et al., Wearable Oximetry for Harsh Environments, IEEE, 2017, 4 pages.

Tilmanne, et al., Algorithms for sleep-wake identification using actigraphy: a comparative study and new results, European Sleep Research Society, Sep. 2008, 14 pages.

Tusman, et al., Photoplethysmographic characterization of vascular tone mediated changes in arterial pressure: an observational study, Journal of Clinical Monitoring and Computing, 2019, 10 pages, vol. 33.

Vetter, et al., Frequency Domain SpO2 Estimation Based on Multichannel Photoplethysmographic Measurements at the Sternum, IFMBE Proceedings, 2009, 4 pages, vol. 25.

Zakeri, et al., Analyzing Seismocardiogram Cycles to Identify the Respiratory Phases, IEEE Transactions on Biomedical Engineering, Aug. 2017, 7 pages, vol. 64 No. 8.

Zheng, et al., Low Ferfusion Algorithm used in Wearable Oximeter and Hardware Acceleration, IEEE, 2016, 5 pages.

Klum, et al., Wearable Cardiorespiratory Monitoring Employing a Multimodal Digital Patch Stethoscope: Estimation of ECG, PEP, LVET and Respiration Using a 55 mm Single-Lead ECG and Phonocardiogram, Sensors, Apr. 2020, 21 pages, vol. 20.

Semiz, et al., Non-Invasive Wearable Patch Utilizing Seismocardiography for Peri-Operative Use in Surgical Patients, IEEE, 2020, 11 pages.

Kwon, et al., Recent advances in wearable sensors and portable electronics for sleep monitoring, iScience, May 2021, 16 pages, vol. 24.

Ganti, et al., Wearable Cuff-less Blood Pressure Estimation at Home via Pulse Transit Time, IEEE Journal of Biomedical and Health Informatics, 2020, 12 pages.

Ha, et al., A Chest-Laminated Ultrathin and Stretchable E-Tattoo for the Measurement of Electrocardiogram, Seismocardiogram, and Cardiac Time Intervals, Advanced Science, 2019, 13 pages, vol. 6.

Jortberg, et al., a novel adhesive biosensor system for detecting respiration, cardiac, and limb movement signals during sleep: validation with polysomnography, Nature and Science of Sleep, 2018, 12 pages, vol. 10.

Javaid, et al., Quantifying and Reducing Motion Artifacts in Wearable Seismocardiogram Measurements during Walking to Assess Left Ventricular Health, IEEE TBME, 2017, 9 pages.

Morillo, et al., Monitoring and Analysis of Cardio Respiratory and Snoring Signals by using an Accelerometer, IEEE EMBS, Aug. 2007, 4 pages.

Solà, et al., On the reliability of pulse oximetry at the sternum, IEEE Embs, Aug. 2007, 1 page.

"510(k) Premarket Notification." Accessdata.fda.gov, U.S. Department of Health & Human Services, Aug. 22, 2022, https://www.accessdata.fda.gov/scripts/cdrh/cfdocs/cfpmn/pmn.cfm?l.

FDA U.S. Food & Drug Administration. "Letter re: K213007, Trade/Device Name: Cerebra Sleep System . . . " Jul. 6, 2022, 17 pages.

U.S. Department of Health & Human Services. "Letter re: K162627, Trade/Device Name: EnsoSleep . . . " Mar. 31, 2017, 7 pages.

FDA U.S. Food & Drug Administration. "Letter re: K210034, Trade/Device Name: EnsoSleep . . . " May 2021, 24 pages.

Davies, Charles, et al., "A Single Arm, Open-Label, Multi-Center, and Comparative Study of the ANNE Sleep System versus Polysomnography to Diagnose Obstructive Sleep Apnea." Journal of Clinical Sleep Medicine : JCSM : Official Publication of the American Academy of Sleep Medicine, U.S. National Library of Medicine, https://pubmed.ncbi.nlm.nih.gov/35934926/.

Younes Sleep Technologies. "Traditional 510(k) Summary K112102 Michelle Sleep Scoring System." Oct. 16, 2011, 16 pages.

U.S. Department of Health & Human Services. "Letter re: K142988, Trade/Device Name: Sleepware G3 . . . " Mar. 16, 2015, 8 pages.

FDA U.S. Food & Drug Administration. "Letter re: K202142, Trade/Device Name: Sleepware G3 . . . " Oct. 29, 2020, 9 pages.

Barker, Signal Extraction Technology, Nov. 30, 2009, 45 pages.

Bicen, et al., A Signal Quality Index for Ballistocardiogram Recordings based on Electrocardiogram RR Intervals and Matched Filtering, IEEE EMBS International Conference on Biomedical & Health Informatics (BHI), Mar. 2018, 4 pages, Las Vegas.

Biometrics, et al., Medical electrical equipment—Part 2-61: Particular requirements for basic safety and essential performance of pulse oximeter equipment, International Standard, 2018, 100 pages, vol. 2.0, Geneva.

Boe, et al., Automating sleep stage classification using wireless wearable sensors, npj Digital Medicine, 2019, 9 pages.

(56) References Cited

OTHER PUBLICATIONS

Brüser, et al., Ambient and Unobtrusive Cardiorespiratory Monitoring Techniques, IEEE Reviews in Biomedical Engineering, 2015, 14 pages, vol. 8.
Bsoul, et al., Real-Time Sleep Quality Assessment Using Single-Lead ECG and Multi-Stage SVM Classifier, IEEE, Sep. 2010, 4 pages, Buenos Aires.
Bsoul, et al., Apnea MedAssist: Real-time Sleep Apnea Monitor Using Single-Lead ECG, IEEE Transactions on Information Technology in Biomedicine, May 2011, 12 pages, vol. 15.
Budidha, et al., Investigation of Pulse Transit Times utilizing multisite reflectance photoplethysmography under conditions of artificially induced peripheral vasoconstriction. 2014 36th Annual International Conference of the IEEE Engineering in Medicine and Biology Society (EMBC), pp. 1965-1968. doi: 10.1109/EMBC. 2014.6943998.
Budidha, et al., Investigation of photoplethysmography and arterial blood oxygen saturation from the ear-canal and the finger under conditions of artificially induced hypothermia, IEEE Engineering in Medicine and Biology Society Conference, Aug. 2015, 5 pages.
Budidha, et al., Photoplethysmography for Quantitative Assessment of Sympathetic Nerve Activity (SNA) During Cold Stress, Front, Physiol, 9:1863, 2019, 10 pages, doi: 10.3389/fphys.2018.01863.
Carek, et al., SeismoWatch: Wearable Cuffless Blood Pressure Monitoring Using Pulse Transit Time, Proc. ACM Interact. Mob. Wearable Ubiquitous Technol. 1, 3, Article 40, Sep. 2017, 16 pages.
Castiglioni, et al., Seismocardiography While Sleeping at High Altitude, IEEE EMBS, Aug. 2012, 4 pages.
Choudhary, et al., Automatic Detection of Aortic Valve Opening Using Seismocardiography in Healthy Individuals, IEEE Journal of Biomedical and Health Informatics, May 2019, 9 pages, vol. 23, No. 3.
Chreiteh, Investigation of Sternal Photoplethysmography—Design of a Vital Sign Patch, Technical University of Denmark, Mar. 2016, 187 pages.
Clifford, et al., Signal Processing Methods for Heart Rate Variability, St. Cross College, 2002, 244 pages.
Clifford, et al., Signal quality in cardiorespiratory monitoring, Physiol. Meas. 33 E01, 2012, 6 pages.
Dassel, et al., Effect of location of the sensor on reflectance pulse oximetry, British Journal of Obstetrics and Gynaecology, Aug. 1997, pp. 910-916, vol. 104.
Dehkordi, et al., Comparison of Different Methods for Estimating Cardiac Timings: A Comprehensive Multimodal Echocardiography Investigation, Front. Physiol. 10:1057, Aug. 2019, 11 pages.
Di Rienzo, et al., Wearable seismocardiography: Towards a beat-by-beat assessment of cardiac mechanics in ambulant subjects, Autonomic Neuroscience: Basic and Clinical, Apr. 2013, 10 pages.
Etemadi, et al., Non-Invasive Assessment of Cardiac Contractility on a Weighing Scale, IEEE EMBS, Sep. 2009, 4 pages.
Etemadi, et al., A Wearable Patch to Enable Long-Term Monitoring of Environmental, Activity and Hemodynamics Variables, IEEE Transactions on Biomedical Circuits and Systems, 2016, 9 pages.
Etemadi, et al., Wearable Ballistocardiogram and Seismocardiogram Systems for Health and Performance, Press. J Appl Physiol, Aug. 2017, 35 pages.
Fonseca, et al., Sleep stage classification with ECG and respiratory effort, Physiological Measurement, 2015, 15 pages, vol. 36.
Gao, et al., Obstructive sleep apnea syndrome detection based on ballistocardiogram via machine learning approach, Mathematical Biosceinces and Engineering, Jun. 2019, 15 pages.
Goldman, et al., Masimo Signal Extraction Pulse Oximetry, Journal of Clinical Monitoring and Computing, Jan. 2000, 9 pages, vol. 16, Kluwer Academic Publishers, Netherlands.
Graybeal, et al., Adaptive Filtering and Alternative Calculations Revolutionizes Pulse Oximetry Sensitivity and Specificity During Motion and Low Perfusion, IEEE EMBS, Sep. 2004, 4 pages.
Gupta, et al., Precision wearable accelerometer contact microphones for longitudinal monitoring of mechano-acoustic cardiopulmonary signals, npj Digital medicine, 2020, 8 pages.
Haahr, et al., An Electronic Patch for Wearable Health Monitoring by Reflectance Pulse Oximetry, IEEE Transactions on Biomedical Circuits and Systems, Feb. 2012, 9 pages, vol. 6 No. 1.
Hartmann, et al., Quantitative Comparison of Photoplethysmographic Waveform Characteristics: Effect of Measurement Site, front. Physiol., Mar. 2019, 8 pages.
He, et al., Secondary Peak Detection of PPG Signal for Continuous Cuffless Arterial Blood Pressure Measurement, IEEE Transactions on Instrumentation and Measurement, Jun. 2014, 9 pages.
Hossein, et al., Accurate Detection of Dobutamineinduced Haemodynamic Changes by Kino-Cardiography: A Randomised Double-Blind placebo-Controlled Validation study, Scientific Reports, Jul. 2019, 11 pages.
Hsu, et al., Screening of obstructive sleep apnea in patients who snore using a patch-type device with electrocardiogram and 3-axis accelerometer, Journal of Clinical Sleep Medicine, 2020, 12 pages.
Hung, Central Sleep Apnea Detection Using an Accelerometer, Association for Computing Machinery, Jun. 2018, 6 pages.
Hung, et al., Estimation of Respiratory Waveform Using an Accelerometer, IEEE ISBI, 2008, 4 pages.
Inan, Wearable Sensing of Left Ventricular Function, Spring International Publishing, Mobile Health, 2017, 23 pages.
Inan, et al., Ballistocardiography and Seismocardiography: A Review of Recent Advances, IEEE Journal of Biomedical and Health Informatics, 2014, 30 pages.
Inan, et al., Novel Wearable Seismocardiography and Machine Learning Algorithms Can Assess Clinical Status of Heart Failure Patients, Circ Heart Fail., 2018, 10 pages.
Inan, et al., Evaluating the Lower-Body Electromyogram Signal Acquired From the Feet As a Noise Reference for Standing Ballistocardiogram Measurements, IEEE Transactions on Information Technology in Biomedicine, Sep. 2010, 9 pages, vol. 14 No. 5.
Javaid, et al., Quantification of Posture Induced Changes in Wearable Seismocardiogram Signals for Heart Failure Patients, Computing in Cardiology, 2016, 4 pages, vol. 43.
Jensen, Signal Processing of Nano Sensor Data, Kongens Lyngby, Mar. 2009, 127 pages.
Jensen, et al., Independent Component Analysis Applied to Pulse Oximetry in the Estimation of the Arterial Oxygen Saturation (SpO2)—a Comparative Study, IEEE EMBS, Sep. 2009, 7 pages.
Johnston, Development of a Signal Processing Library for Extraction of SpO2, HR, HRV, and RR from Photoplethysmographic Waveforms, Worcester Polytechnic Institute, 2006, 148 pages.
Khosrow-Khavar, et al., Automatic and Robust Delineation of the Fiducial Points of the Seismocardiogram Signal for Noninvasive Estimation of Cardiac Time Intervals, IEEE Transactions on Biomedical Engineering, Aug. 2017, 10 pages, vol. 64. No. 8.
Kramer, et al., Wearable Pulse Oximetry Measurements on the Torso, Arms, and Legs: A Proof of Concept, Military Medicine, 2017, 7 pages.
Li, et al., Principle Component Analysis on Photoplethysmograms: Blood Oxygen Saturation Estimation and Signal Segmentation, IEEE EMBS, Sep. 2011, 4 pages.
Liang, et al., Analysis: An optimal filter for short photoplethysmogram signals, Scientific Data, May 2018, 12 pages.
Longmore, et al., A Comparison of Reflective Photoplethysmography for Detection of Heart Rate, Blood Oxygen Saturation, and Respiration Rate at Various Anatomical Locations, Sensors, Apr. 2019, 19 pages.
Mendelson, et al., Noninvasive Pulse Oximetry Utilizing Skin Reflectance Photoplethysmography, IEEE Transactions on Biomedical Engineering, Oct. 1988, 8 pages, vol. 35 No. 10.
Morra, et al., Modification of the mechanical cardiac performance during end-expiratory voluntary apnea recorded with ballistocardiography and seismocardiography, Physiological Measurement, 2019, 32 pages.
Morra, et al., Ballistocardiography and Seismocardiography detect hemodynamic changes during simulated obstructive apnea, Physiological Measurement, 2020, 34 pages.

\* cited by examiner

SYSTEMS AND PROCESSES FOR DETECTING OXYGEN SATURATION AND COMPENSATING FOR SKIN TONE VARIATION

CROSS-REFERENCE TO RELATED APPLICATIONS

This application:

claims priority to and the benefit of U.S. Provisional Patent Application No. 63/496,264, filed Apr. 14, 2023, entitled "DYNAMIC PPG SKIN TONE COMPENSATION SYSTEMS AND PROCESSES"; and is a continuation-in-part of U.S. patent application Ser. No. 18/402,925, filed Jan. 3, 2024, entitled "HEART FAILURE DETECTION DEVICES, SYSTEMS, AND PROCESSES," which claims priority to and the benefit of U.S. Provisional Patent Application No. 63/478,494, filed Jan. 4, 2023, entitled "HEART FAILURE DETECTION DEVICES, SYSTEMS, AND PROCESSES," and is a continuation-in-part of U.S. patent application Ser. No. 18/299,539, filed Apr. 12, 2023, entitled "PROCESSING AND ANALYZING BIOMETRIC DATA," which is a continuation of U.S. patent application Ser. No. 17/833,894, filed Jun. 6, 2022, entitled "PROCESSING AND ANALYZING BIOMETRIC DATA," now U.S. Pat. No. 11,660,005, which claims priority to U.S. Provisional Patent Application No. 63/196,778, filed Jun. 4, 2021, entitled "PROCESSING AND ANALYZING BIOMETRIC DATA," each of the above are incorporated herein by reference in their entireties.

GOVERNMENT LICENSE RIGHTS

This invention was made with government support under NSF Award ID 2136470 awarded by the National Science Foundation. The government has certain rights in the invention.

BACKGROUND

Photoplethysmography (PPG) sensors may be used for detecting and monitoring a patient's heart rate. However, the signal quality of the PPG sensors may vary depending on the patient and location of the PPG sensor. As one example, PPG signal quality may decrease for those patients with highly pigmented skin and/or with a higher body mass index (BMI) (e.g., greater than 30). As another example, PPG signal quality may have a high signal-to-noise ratio (SNR) on the patient's chest.

BRIEF DESCRIPTION OF THE DISCLOSURE

In various embodiments, the present disclosure provides systems and processes for improving and optimizing PPG signal quality for estimating patients' oxygen saturation (SpO2). As will be understood, PPG signal quality is particularly susceptible to noise on a patient's chest, making separating peaks and troughs of the PPG waveform associated with the pulsatile component of blood flow from peaks and troughs due to noise (movement, respiration, etc.) challenging. However, eliminating noise from the PPG signal and determining accurate peaks (e.g., amplitude) can be particularly important for precisely estimating a patient's SpO2 percentage.

Further, the present disclosure includes systems and processes for improving and optimizing PPG signal quality based on highly pigmented skin and/or a high BMI. As will be understood, highly pigmented skin and/or high BMI can affect PPG signal quality and thus SpO2 percentage estimates and other computations.

According to a first aspect, the present disclosure includes a system for deriving an estimated oxygen saturation percentage (SpO2%) for a patient comprising: a patch configured for attaching to skin of a patient and comprising: a photoplethysmography (PPG) sensor for providing reflectance red data and infrared (IR) data; a heartbeat detector comprising electrocardiogram (ECG) sensor, an accelerometer, a bioimpedance sensor, and/or a beat detector for providing a series of heartbeats; and a radio for transmitting the red data, the IR data, and the series of heartbeats, wherein the red data, the IR data, and the series of heartbeats are associated with a time period; and a processor configured to: receive, from the radio, the red data, the IR data, and the series of heartbeats associated with the time period; compute a series of peaks of the red data and IR data for the time period; compute a subset of the red data and IR data by excluding any peaks of the series of peaks that do not correspond with a heartbeat of the series of heartbeats, thereby verifying peaks for the red data and IR data from the patch attached to the patient's chest and eliminating potential noise and false peaks; estimate an oxygen saturation percentage (SpO2%) for the patient by computing an optical ratio of the red data and IR data included in the subset; and display on a computer screen the estimated SpO2% for the patient.

In a second aspect of the system of the first aspect or any other aspect, wherein: the subset of the red data and IR data comprises a particular peak of the series of peaks at a particular time; the series of heartbeats includes a particular heartbeat occurring within a predetermined window of the particular time; and the estimated SpO2% for the patient is based on the particular peak.

In a third aspect of the system of the first aspect or any other aspect, wherein: each peak of the series of peaks corresponds with a specific time of the time period; and a specific peak of the series of peaks does not correspond with a heartbeat of the series of heartbeats if there is no heartbeat within a predetermined window of the specific time corresponding with the specific peak.

In a fourth aspect of the system of the second aspect or any other aspect, wherein the processor is configured to estimate the SpO2% by: splitting the subset of the red data and IR data into alternating current (AC) and direct current (DC) components; and estimating the patient's SpO2% by the optical ratio expressed as:

$$R = \frac{AC_{rms\,RED} / DC_{rms\,RED}}{AC_{rms\,IR} / AC_{rms\,IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

In a fifth aspect of the system of the fourth aspect or any other aspect, wherein the time period is derived from a single clock or two or more synchronized clocks.

According to a sixth aspect, the present disclosure includes a system for deriving an estimated oxygen saturation percentage (SpO2%) for a patient comprising: at least one processor communicably coupled to a patch for affixing to a patient and configured to: receive reflectance red data and IR data derived from a photoplethysmography (PPG) sensor coupled to the patch and associated with a time period; receive a series of heartbeats associated with the time period and derived from a heartbeat detector, the heartbeat detector comprising an electrocardiogram (ECG) sensor, an accelerometer, bioimpedance sensor, and/or a beat detector coupled to the patch; compute a series of peaks of the red data and IR data for the time period; compute a subset of the red data and IR data by excluding any peaks of the series of peaks that do not fall within a predetermined time window of a heartbeat of the series of heartbeats; estimate an oxygen saturation percentage (SpO2%) for the patient by computing an optical ratio of the red data and IR data included in the subset, thereby verifying peaks for the red data and IR data from the patch attached to the patient's chest and eliminating potential noise and false peaks; and display on a computer screen the estimated SpO2% for the patient.

In a seventh aspect of the system of the sixth aspect or any other aspect, wherein the red data, the IR data, and the series of heartbeats are associated with the time period via one or more clocks of a processor coupled to the patch.

In an eighth aspect of the system of the seventh aspect or any other aspect, wherein: the subset of the red data and the IR data comprises a particular peak of the series of peaks at a particular time; the series of heartbeats includes a particular heartbeat occurring within the predetermined time window of the particular time; and the estimated SpO2% for the patient is based on the particular peak.

In a ninth aspect of the system of the seventh aspect or any other aspect, wherein: each peak of the series of peaks corresponds with a specific time of the time period; and a specific peak of the series of peaks does not correspond with a heartbeat of the series of heartbeats if there is no heartbeat within the predetermined time window of the specific time corresponding with the specific peak.

In a tenth aspect of the system of the eighth aspect or any other aspect, wherein the at least one processor is configured to estimate the SpO2% by: splitting the subset into alternating current (AC) and direct current (DC) components for the red data and the IR data; and estimating the patient's SpO2% by the optical ratio expressed as:

$$R = \frac{AC_{rms\ RED}/DC_{rms\ RED}}{AC_{rms\ IR}/AC_{rms\ IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

According to an eleventh aspect, the present disclosure includes a system for deriving an estimated oxygen saturation percentage (SpO2%) for a patient comprising: at least one processor communicably coupled to a patch for affixing to a patient and configured to: receive reflectance red data and IR data derived from a photoplethysmography (PPG) sensor coupled to the patch; receive a series of heartbeats derived from a heartbeat detector; compute a series of peaks of the red data and IR data for a time period; compute a subset of the red data and IR data by excluding any peaks of the series of peaks that do not fall within a predetermined time window of a heartbeat of the series of heartbeats, wherein the series of heartbeats are associated with the time period; estimate an oxygen saturation percentage (SpO2%) for the patient by computing an optical ratio of the red data and IR data included in the subset, thereby verifying peaks for the red data and IR data from the patch attached to the patient's chest and eliminating potential noise and false peaks; and display on a computer screen the estimated SpO2% for the patient.

In a twelfth aspect of the system of the eleventh aspect or any other aspect, wherein the heartbeat detector comprises an electrocardiogram (ECG) sensor, an accelerometer, bioimpedance sensor, and/or a beat detector.

In a thirteenth aspect of the system of the twelfth aspect or any other aspect, wherein the heartbeat detector is coupled to the patch.

In a fourteenth aspect of the system of the thirteenth aspect or any other aspect, wherein the series of heartbeats are associated with the time period via a processor coupled to the patch.

In a fifteenth aspect of the system of the fourteenth aspect or any other aspect, wherein the red data, the IR data, and the series of heartbeats are associated with the time period via one or more clocks of the processor coupled to the patch.

In a sixteenth aspect of the system of the eleventh aspect or any other aspect, wherein: the PPG sensor is a first PPG sensor; and the heartbeat detector is a second PPG sensor.

In a seventeenth aspect of the system of the sixteenth aspect or any other aspect, wherein the series of heartbeats are associated with the time period via synchronizing a second PPG sensor time period with the time period based on pulse transit time for the patient.

In an eighteenth aspect of the system of the eleventh aspect or any other aspect, wherein: the subset of the red data and the IR data comprises a particular peak of the series of peaks at a particular time; the series of heartbeats includes a particular heartbeat occurring within the predetermined time window of the particular time; and the estimated SpO2% for the patient is based on the particular peak.

In a nineteenth aspect of the system of the eleventh aspect or any other aspect, wherein: each peak of the series of peaks corresponds with a specific time of the time period; and a specific peak of the series of peaks does not correspond with a heartbeat of the series of heartbeats if there is no heartbeat within the predetermined time window of the specific time corresponding with the specific peak.

In a twentieth aspect of the system of the eleventh aspect or any other aspect, wherein the at least one processor is configured to estimate the SpO2% by: splitting the subset into alternating current (AC) and direct current (DC) components for the red data and the IR data; and estimating the patient's SpO2% by the optical ratio expressed as:

$$R = \frac{AC_{rms\ RED}/DC_{rms\ RED}}{AC_{rms\ IR}/AC_{rms\ IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

According to a twenty-first aspect, the present disclosure includes a process for deriving an estimated oxygen saturation percentage (SpO2%) for a patient comprising: receiving, from a processor attached to a patient's chest, red data, infrared (IR) data, and a series of heartbeats for a time period, wherein: the processor is communicably coupled to: a photoplethysmography (PPG) sensor for providing the red data and IR data via at least one red light-emitting diode (LED), at least one IR LED, and at least one photodiode; an electrocardiogram (ECG) sensor, an accelerometer, and/or a beat detector for providing the series of heartbeats; and the processor uses one or more synchronized clocks to associate the red data, the IR data, and the series of heartbeats with the time period; computing a series of peaks of the red data and IR data for the time period; computing a subset of the red data and IR data by excluding any peaks of the series of peaks that do not correspond with a heartbeat of the series of heartbeats, thereby verifying peaks for the red data and IR data from the PPG sensor attached to the patient's chest and eliminating potential noise and false peaks; estimating an oxygen saturation percentage (SpO2%) for the patient by computing an optical ratio of the red data and IR data included in the subset; and displaying on a computer screen the estimated SpO2% for the patient.

In a twenty-second aspect of the process of the twenty-first aspect or any other aspect, wherein: the subset of the red data and IR data comprises a particular peak of the series of peaks at a particular time; the series of heartbeats comprise a particular heartbeat occurring within a predetermined window of the particular time; and the estimated SpO2% for the patient is based on the particular peak.

In a twenty-third aspect of the process of the twenty-first aspect or any other aspect, wherein: each peak of the series of peaks corresponds with a specific time of the time period; and a specific peak of the series of peaks does not correspond with a heartbeat of the series of heartbeats if there is no heartbeat within a predetermined window of the specific time corresponding with the specific peak.

In a twenty-fourth aspect of the process of the twenty-second aspect or any other aspect, wherein estimating SpO2% for the patient comprises: splitting the subset of the red data and IR data into alternating current (AC) and direct current (DC) components; and estimating the patient's SpO2% by the optical ratio expressed as:

$$R = \frac{AC_{rms\ RED} / DC_{rms\ RED}}{AC_{rms\ IR} / AC_{rms\ IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

In a twenty-fifth aspect of the process of the twenty-fourth aspect or any other aspect, wherein the processor assigns time data to the red data, IR data, and series of heartbeats from a single clock or from multiple, synchronized clocks.

According to a twenty-sixth aspect, the present disclosure includes a process for deriving an estimated oxygen saturation percentage (SpO2%) for a patient comprising: receiving red data and infrared (IR) data for a time period from a photoplethysmography (PPG) sensor attached to the patient's chest, wherein the PPG sensor receives the red data and IR data via at least one red light-emitting diode (LED), at least one IR LED, and at least one photodiode; deriving a series of heartbeats from data received from a second sensor other than the PPG sensor, for the time period, wherein each heartbeat of the series of heartbeats is associated with a particular time of the time period; determining a series of peaks of the red data and IR data for the time period; and displaying on a computer screen an estimated oxygen saturation percentage (SpO2%) for the patient based on red data and IR data for a subset of the time period that excludes one or more peaks of the series of peaks of the red data and IR data that do not occur within a predetermined window of a heartbeat of the series of heartbeats, thereby verifying peaks for the red data and IR data from the PPG sensor attached to the patient's chest and eliminating potential noise and false peaks.

In a twenty-seventh aspect of the process of the twenty-sixth aspect or any other aspect, wherein: the red data and IR data for the subset of the time period include a particular peak of the series of peaks at the particular time; the series of heartbeats includes a particular heartbeat occurring within the predetermined window of the particular time; and the estimated SpO2% for the patient is based on the particular peak.

In a twenty-eighth aspect of the process of the twenty-seventh aspect or any other aspect, wherein the red data and IR data for the subset of the time period further excludes a first peak of the series of peaks that: corresponds to a first heartbeat of the heartbeat data; and is not adjacent to a second peak of the series of peaks.

In a twenty-ninth aspect of the process of the twenty-eighth aspect or any other aspect, wherein: the red data and IR data for the subset of the time period comprise a dataset; the estimated SpO2% for the patient is based on: splitting the dataset into alternating current (AC) and direct current (DC) components for the red data and the IR data; and estimating the patient's SpO2% by an optical ratio expressed as:

$$R = \frac{AC_{rms\ RED} / DC_{rms\ RED}}{AC_{rms\ IR} / AC_{rms\ IR}}$$

wherein R represents the optical ratio, ACrms RED represents the root means square of the red AC data of the dataset, DCrms RED represents the root means square of the red DC data of the dataset, ACrms IR represents the root means square of the IR AC data of the dataset, and DCrms IR represents the root means square of the IR DC data of the dataset.

In a thirtieth aspect of the process of the twenty-ninth aspect or any other aspect, wherein the second sensor is an electrocardiogram (ECG) sensor.

In a thirty-first aspect of the process of the thirtieth aspect or any other aspect, wherein: the PPG sensor and the ECG sensor are communicably coupled to a processor attached to the patient's chest; and the processor assigns time data to the red data, IR data, and series of heartbeats from one or more clocks.

In a thirty-second aspect of the process of the twenty-ninth aspect or any other aspect, wherein: the second sensor is an accelerometer; the PPG sensor and the accelerometer are communicably coupled to a processor attached to the patient's chest; and the processor assigns time data to the red data, IR data, and series of heartbeats from one or more clocks.

In a thirty-third aspect of the process of the twenty-ninth aspect or any other aspect, wherein: the second sensor is a beat detector; the PPG sensor and the beat detector are communicably coupled to a processor attached to the patient's chest; and the processor assigns time data to the red data, IR data, and series of heartbeats from one or more clocks.

In a thirty-fourth aspect of the process of the twenty-ninth aspect or any other aspect, wherein: the second sensor is a bioimpedance sensor; the PPG sensor and the bioimpedance sensor arc communicably coupled to a processor attached to the patient's chest; and the processor assigns time data to the red data, IR data, and series of heartbeats from one or more clocks.

In a thirty-fifth aspect of the process of the twenty-ninth aspect or any other aspect, wherein: the second sensor is a second PPG sensor attached to the patient; and the process further comprises converting time data for the second PPG sensor to the time period based on pulse transit time.

According to a thirty-sixth aspect, the present disclosure includes a process for optimizing photoplethysmography (PPG) data derived from a patient with highly pigmented skin and/or a high body mass index comprising: determining, via at least one processor, whether a red drive current and/or infrared (IR) drive current meet a maximum threshold or a minimum threshold; upon determining that one of the red drive current and IR drive current are not at the maximum threshold or the minimum threshold, adjusting a plurality of light-emitting diodes (LEDs); determining whether an intensity associated with the red drive current and/or IR drive current is in a set range; upon determining that the intensity associated with one of the red drive current and IR drive current is not in the set range, determining whether the red drive current and/or infrared (IR) drive current meet the maximum threshold or the minimum threshold; upon determining that one of the red drive current and IR drive current are at the maximum threshold or the minimum threshold, adjusting an analog-to-digital full scale range (ADC FSR); resetting a light intensity of the LEDs by adjusting the LEDs; and adjusting a force applied via a photoplethysmography (PPG) sensor onto a patient's skin, the PPG sensor comprising the LEDs.

According to a thirty-seventh aspect, the present disclosure includes a system for optimizing photoplethysmography (PPG) data derived from a patient with highly pigmented skin and/or a high body mass index: at least one processor configured to: determine, via at least one processor, whether a red drive current and/or infrared (IR) drive current meet a maximum threshold or a minimum threshold; upon determining that one of the red drive current and IR drive current are not at the maximum threshold or the minimum threshold, adjust a plurality of light-emitting diodes (LEDs); determine whether an intensity associated with the red drive current and/or IR drive current is in a set range; upon determining that the intensity associated with one of the red drive current and IR drive current is not in the set range, determine whether the red drive current and/or infrared (IR) drive current meet the maximum threshold or the minimum threshold; upon determining that one of the red drive current and IR drive current are at the maximum threshold or the minimum threshold, adjust an analog-to-digital full scale range (ADC FSR); reset a light intensity of the LEDs by adjusting the LEDS; and adjust a force applied via a photoplethysmography (PPG) sensor onto a patient's skin, the PPG sensor comprising the LEDs.

Figure 1:
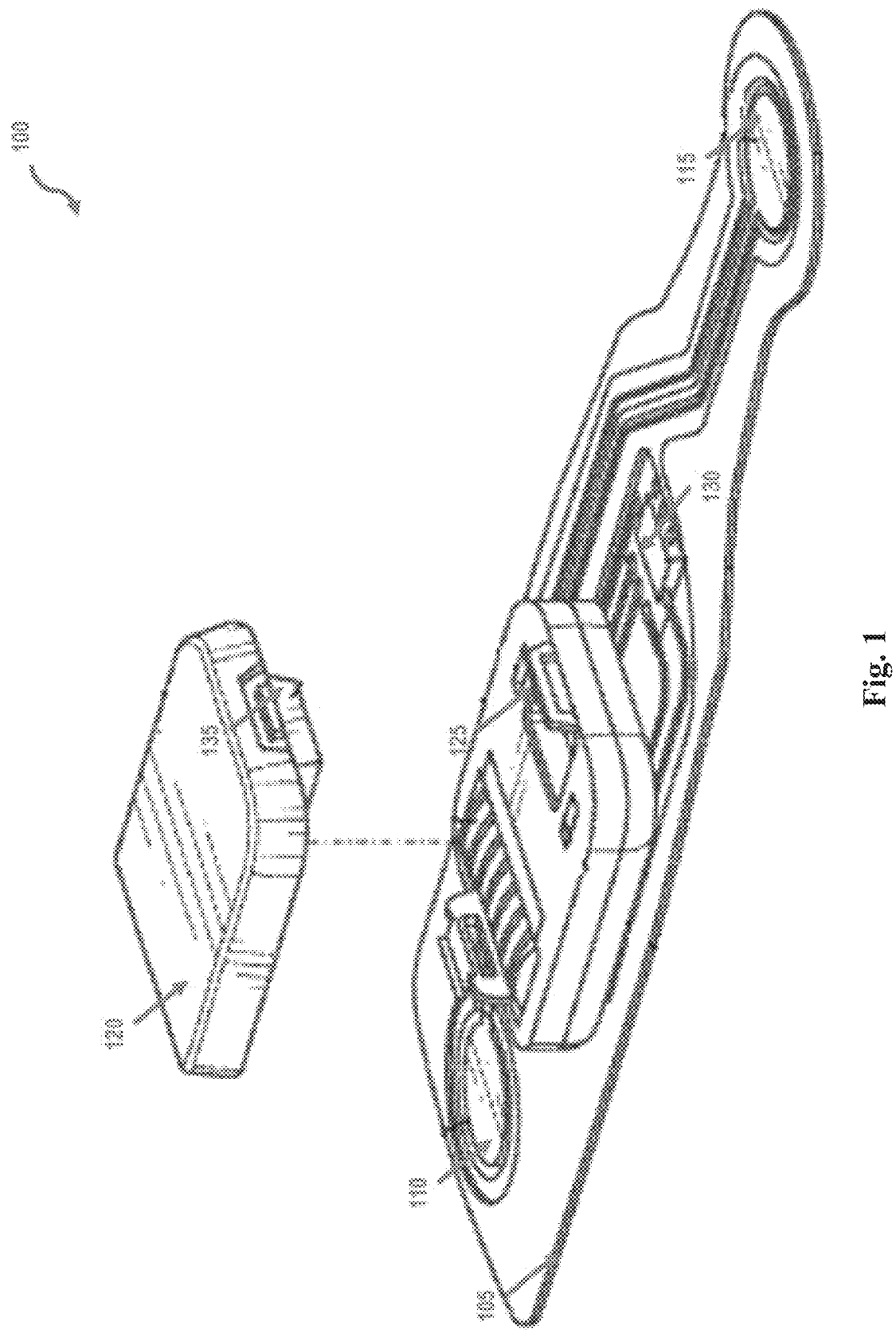
FIG. 1 illustrates a top perspective view of an example patch device according to various embodiments of the present disclosure.

While the disclosure is susceptible to various modifications and alternative forms, a specific embodiment thereof is shown by way of example in the drawings and will herein be described in detail. It should be understood, however, that the drawings and detailed description presented herein are not intended to limit the disclosure to the particular embodi-

DETAILED DESCRIPTION

This disclosure will now be described with reference to the drawing figures, in which like reference numerals refer to like parts throughout. For purposes of clarity in illustrating the characteristics of the present disclosure, proportional relationships of the elements have not necessarily been maintained in the drawing figures.

FIG. 1 illustrates a top perspective view of an example patch device 100 according to various embodiments of the present disclosure. In some embodiments, the patch device 100 is similar to the patch devices described in detail in commonly assigned U.S. patent application Ser. No. 17/199,181 titled "PATCH FOR IMPROVED BIOMETRIC DATA CAPTURE AND RELATED PROCESSES" filed on Mar. 11, 2021 and/or U.S. patent application Ser. No. 18/338,888 titled "PHOTOPLETHYSMOGRAPHY SENSORS AND PROCESSES" filed on Jun. 21, 2023, which are incorporated herein by reference. Relevant to the present disclosure, the patch device 100 can include a flexible circuit layer 105, which may include a bottom adhesive layer, a receptacle cover 120, a battery receptacle 125, and a plurality of sensors. In one embodiment, the bottom adhesive layer of the flexible circuit layer 105, the receptacle cover 120, or the battery receptacle 125 includes a processor or microcontroller that executes the applications as discussed herein and is in communication with the sensors.

The sensors may be used to collect data points. According to at least one embodiment, the sensors collect data from the patch device 100 attached to a patient. The sensors may be wired to the computing system (which will be discussed with reference to FIG. 2 below) or may be wireless. In some embodiments, the sensors may include a first electrocardiogram (ECG) electrode 110, a second ECG electrode 115, a photoplethysmography (PPG) sensor layer 130, and/or an accelerometer 135. The PPG sensor layer 130 may include a PPG sensor. Certain sensors (e.g., PPG, ECG) may produce better (e.g., higher amplitude) or more consistent signals when adhered or pressed against the chest of the patient (even when a chest expands/contracts and/or when a patient rolls during sleep). In various embodiments, it may be advantageous for one or more of these sensors to be coupled to a flexible and/or stretchable substrate (e.g., the flexible circuit layer 105) and otherwise be isolated from rigid components (e.g., a circuit board).

In some embodiments, the sensors include an ECG sensor made up of the first ECG electrode 110 and/or the second ECG electrode 115. In some embodiments, the ECG sensor includes an ECG electrode and a ground.

The ECG electrodes 110 and 115 may have a circular shape with a certain diameter, such as, but not limited to, 15 to 25 millimeters. According to at least one embodiment, the ECG electrodes 110 and 115 may be directly in contact with the patient's skin. When in direct contact, there are no additional layers between the patient's skin and the ECG electrodes 110 and 115. In some embodiments, the ECG sensor is not directly in contact with a patient's skin. In these embodiments (and others), there is a layer of hydrogel (or other suitable material) between the ECG sensor and the patient's skin.

In various embodiments, the ECG sensor is configured to be used by the processor to measure the electrocardiogram on the patch device 100, which can be further used to determine cardiorespiratory parameters. The ECG sensor can read, monitor, and measure electrical activity (e.g., voltage) of a patient's heart over time (among other things). The ECG sensor may detect a heartbeat or other electrical properties of the heart via the voltage changes in the user's heart. The ECG sensor may also include an ECG amplifier. In some embodiments, the ECG sensor can include a two-lead, a three-lead, or other number of lead ECG sensor. The ECG sensor can also include a heart rate sensor and a pulse oximeter.

In one embodiment, the sensors include the PPG sensor in the PPG sensor layer 130. In some embodiments, the PPG sensor interprets data from red and infrared (IR) light. In various embodiments, the PPG sensor is configured to measure at least the patient's pulse rate and pulse rate variability, respiratory rate, and blood flow. The PPG sensor may measure volumetric variations of blood circulation at the surface of the user's skin via optics. The PPG sensor may perform reflectance-mode PPG signal detection of a design and sampling range of 50-200 Hz. In some embodiments, the PPG sensor may be configured to monitor, measure, and/or sense sensor measurements, such as, but not limited to, vasoconstriction, heart rate, SpO2 levels, cutaneous blood flow and volume, which will be discussed further in reference to FIG. 5.

According to at least one embodiment, the PPG sensor can include an array board with a plurality of light emitting diodes (LEDs) and a plurality of photodiodes (PDs). According to one embodiment, the PPG sensor provides red data and IR data via at least one red light-emitting diode (LED), at least one IR LED, and at least one photodiode. In at least one embodiment, a combination of innovations discussed herein (including, but not limited to, peak/heartbeat determination, force adjustment, and PPG adjustment based on skin pigmentation) enable a device/patch with just two LEDs (red and IR) and one photodiode in a singular configuration. Third parties have used arrays of LEDs and photodiodes to overcome signal amplitude issues on low perfusion or high pigmented skin/patients, but the systems, devices, and processes discussed herein overcome the limitations of prior/third-party systems and enable a singular configuration.

The array board may include alternating individual LEDs and PDs on the array board such that each individual LED is proximate to individual PDs, and each individual PD is proximate to individual LEDs. For example, the array board can include a printed circuit board (PCB) with pairs of apertures for leads of a PD or an LED spaced a part at a specific distance. The specific distance may be greater than or equal to 6 mm, 6 mm, 9 mm, 12 mm, or some other distance as can be appreciated.

In various embodiments, the patch device 100 may include an adaptive filter configured to reduce a noise of readings from the plurality of PDs or other components of the patch device 100. The adaptive filter can be applied to a measurement or signal from the PPG sensor and/or the ECG sensor to extract information using frequency-domain or time-domain features. As an example, the adaptive filter can extract beat-to-beat heartbeats from a data signal corresponding to the PPG sensor and/or the ECG sensor.

In one embodiment, the accelerometer 135 is a three-axis accelerometer, which may be wired to the processor. The processor can derive x-axis data, y-axis data, and z-axis data from the three-axis accelerometer and send the data for further processing. As will be understood from discussions herein, in various embodiments, the data corresponds to various measurements of the patient's sleeping position or body orientation. This data may be observed to determine which way the patient is sleeping, which can be useful for determining effects of how the patient sleeps on the patient's respiratory patterns.

In one embodiment, the data is in a binary format when received by the processor. The processor is configured to derive the data using a processing script.

According to at least one embodiment, the patch device 100 can provide a singular continuous area of contact to collect various sensor measurements. This continuous area of contact can limit the impact of inevitable patient movement on the collection of data. Moreover, the continuous area of contact can prevent inaccurate or inconsistent data from being collected from the patient.

Figure 2:
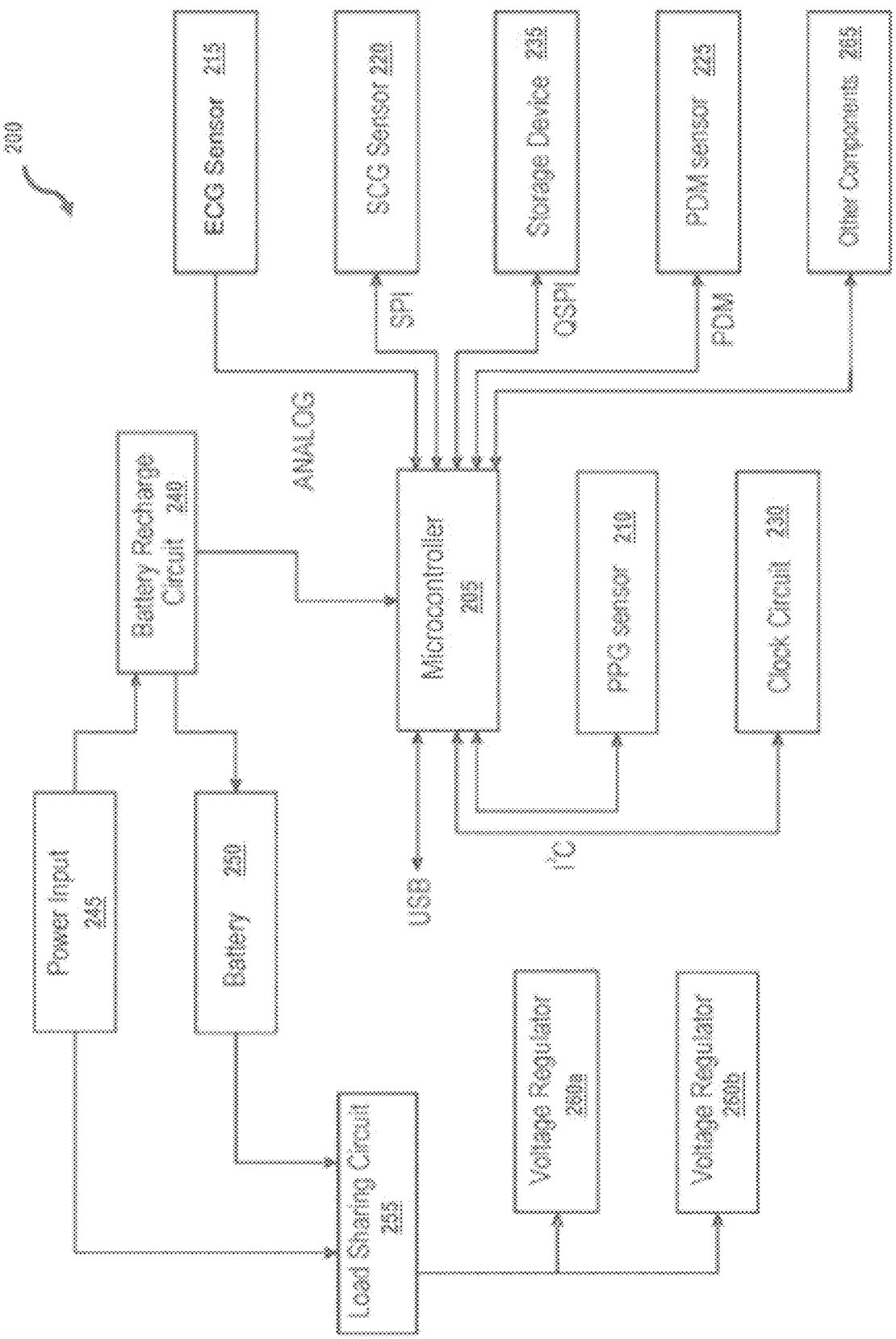
FIG. 2 illustrates a functional circuit diagram for the patch device (as shown in FIG. 1) according to various embodiments of the present disclosure.

FIG. 2 illustrates a functional circuit diagram for the patch device 100 (as shown in FIG. 1) according to various embodiments of the present disclosure and similar to that as described in detail in commonly assigned U.S. patent application Ser. No. 17/199,181 titled "PATCH FOR IMPROVED BIOMETRIC DATA CAPTURE AND RELATED PROCESSES" filed on Mar. 11, 2021, which is incorporated herein by reference. The circuit diagram 200 can include a processor 205 in communication with one or more sensors shown as PPG sensor 210, ECG sensor 215, SCG sensor 220, and PDM sensor 225, among other sensors. The processor 205 can be in communication with a clock circuit 230, a storage device 235, and a battery recharge circuit 240.

In various embodiments, the battery recharge circuit 240 can receive power from a power input 245 and use the received power to charge the battery 250. The power input 245 can be coupled to an external power signal and the battery recharge circuit 240 can store power from the external power signal in the battery 250. The load sharing circuit 255 can provide power from the battery 250 when the battery recharge circuit 240 is not receiving the external power signal and provide the input power signal from the power input 245 when the battery recharge circuit 240 is receiving the external power signal. Stated differently, the load sharing circuit 255 can receive power from either the power input 245, the battery 250, or the power input 245 and the battery 250.

The load sharing circuit 255 can provide a power signal to one or more voltage regulators, such as voltage regulators 260a and 260b. In one embodiment, the voltage regulator 260a can provide a first input voltage to one or more circuit components, and the voltage regulator 260b can provide a second input voltage to one or more other circuit components.

The circuit diagram 200 can include other components 265, which may or may not be coupled directly to the processor 205. The other components 265 can include one or more radio frequency filters coupled to the processor 205 and/or one or more antennas or radios for receiving or transmitting data, which may be coupled to the radio frequency filter. In one embodiment, the other components 265 include a gyroscope. In one embodiment, the other components 265 include an accelerometer. In one embodiment, the other components 265 include a compass. In one embodiment, the other components 265 include a digital motion processor, which can be configured to offload computation of motion processing processes from the processor 205.

Figure 3:
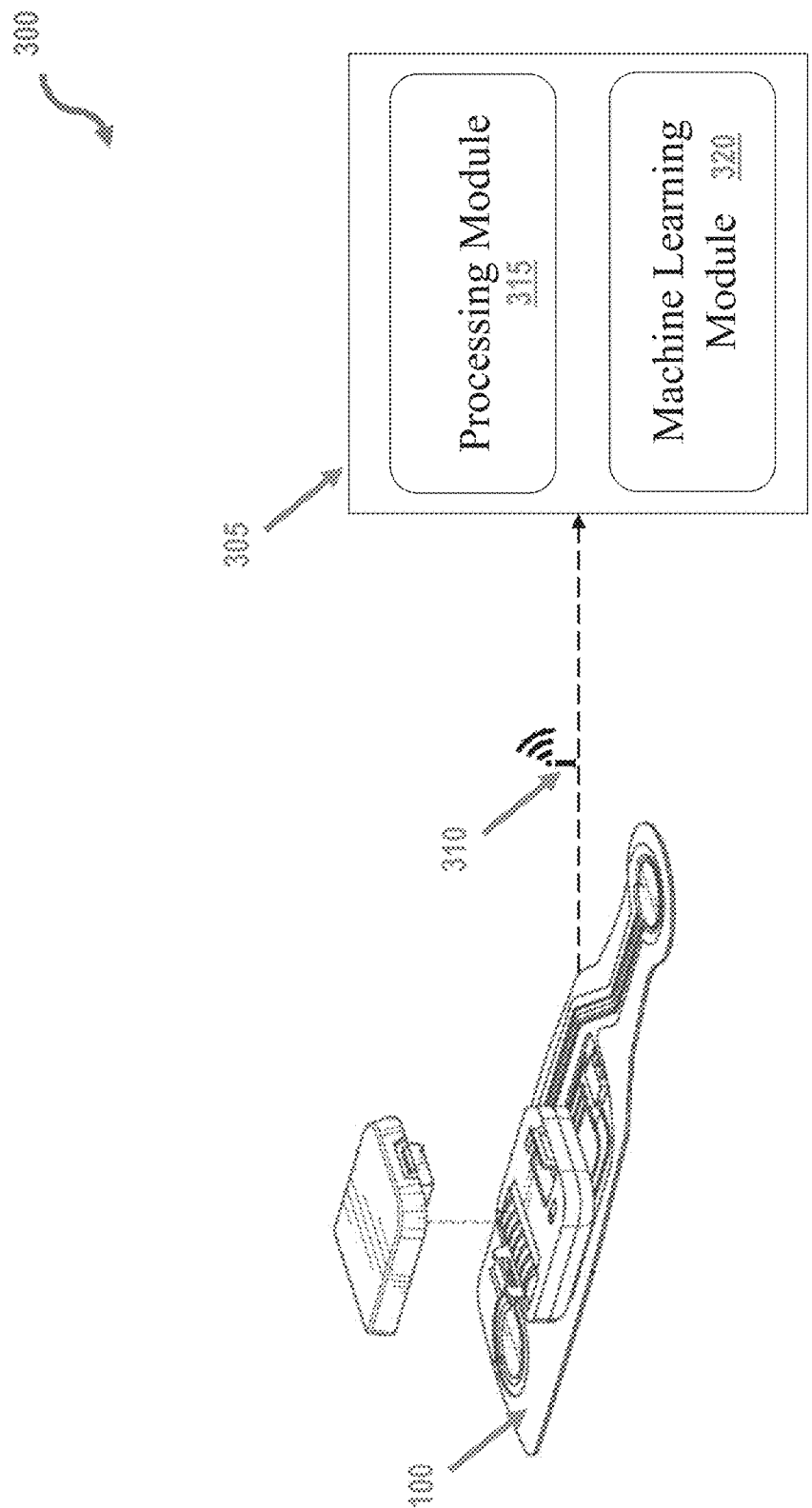
FIG. 3 is a computing architecture diagram illustrating the connection between a patch device and a computing system according to various embodiments of the present disclosure.

FIG. 3 is a computing architecture diagram illustrating the connection between a patch device and a computing system according to various embodiments of the present disclosure. In one embodiment, the patch device is the patch device 100 from FIG. 1.

According to at least one embodiment, the patch device 100 is connected to the computing system 305 via an internet connection 310. In one embodiment, the internet connection 310 allows the data collected from the patch device to be processed and analyzed at the computing system 305.

In one or more embodiments, the patch device is connected to the computing system 305 via another suitable mechanism. For example, after use by a patient, the patch device 100 might be connected to the computing system 305 and data downloaded to the computing system 305 from the patch device 100. Continuing with this example, the patch device 100 might be connected to the computing system 305 via another suitable mechanism, including, but not limited to, a wired connection (e.g., a port connected to the processor, which may be the processor 205 from FIG. 2), a near-field communications connection, a Bluetooth connection, cellular, or a contact connection (e.g., via one or more contacts for data transfer on the patch device 100).

The computing system 305 has a processing module 315 and a machine learning module 320. In one embodiment, the processing module 315 is configured to parse the data collected by the patch device 100 and determine if an issue (e.g., breathing irregularity, sleep position strain, cardiac issues, and respiratory issues) exists based on the parsed data. The data that can be parsed by the processing module will be discussed herein with reference to FIGS. 4 and 5. According to at least one embodiment, the processing module 315 can complete initial processing of various data points. Additionally, the processing module 315 may complete autoscoring, which will be discussed further with reference to FIG. 7.

In one embodiment, the machine learning module 320 is configured to receive the data collected by the patch device 100 and an apnea-hypopnea index (AHI) for the patient whose data was received. The data collected may be raw data in a binary format. In one embodiment, the machine learning module 320 is configured to calculate various features as discussed with reference to FIG. 5. According to at least one embodiment, the machine learning module 320 receives a variety of inputs, trains one or more machine learning models based on known outputs, and predicts diagnoses for the patient based on the correlation between the inputs and known outputs.

As will be understood from discussions herein, the system may receive raw data from the one or more sensors of the patch device 100. The system may then parse the raw data, derive features from the data, and then use the raw data and/or derived features to estimate, compute, or determine one or more characteristics of a patient (e.g., a likelihood of sleep apnea, a AHI score, etc.), each of which will be discussed below.

Figure 4:
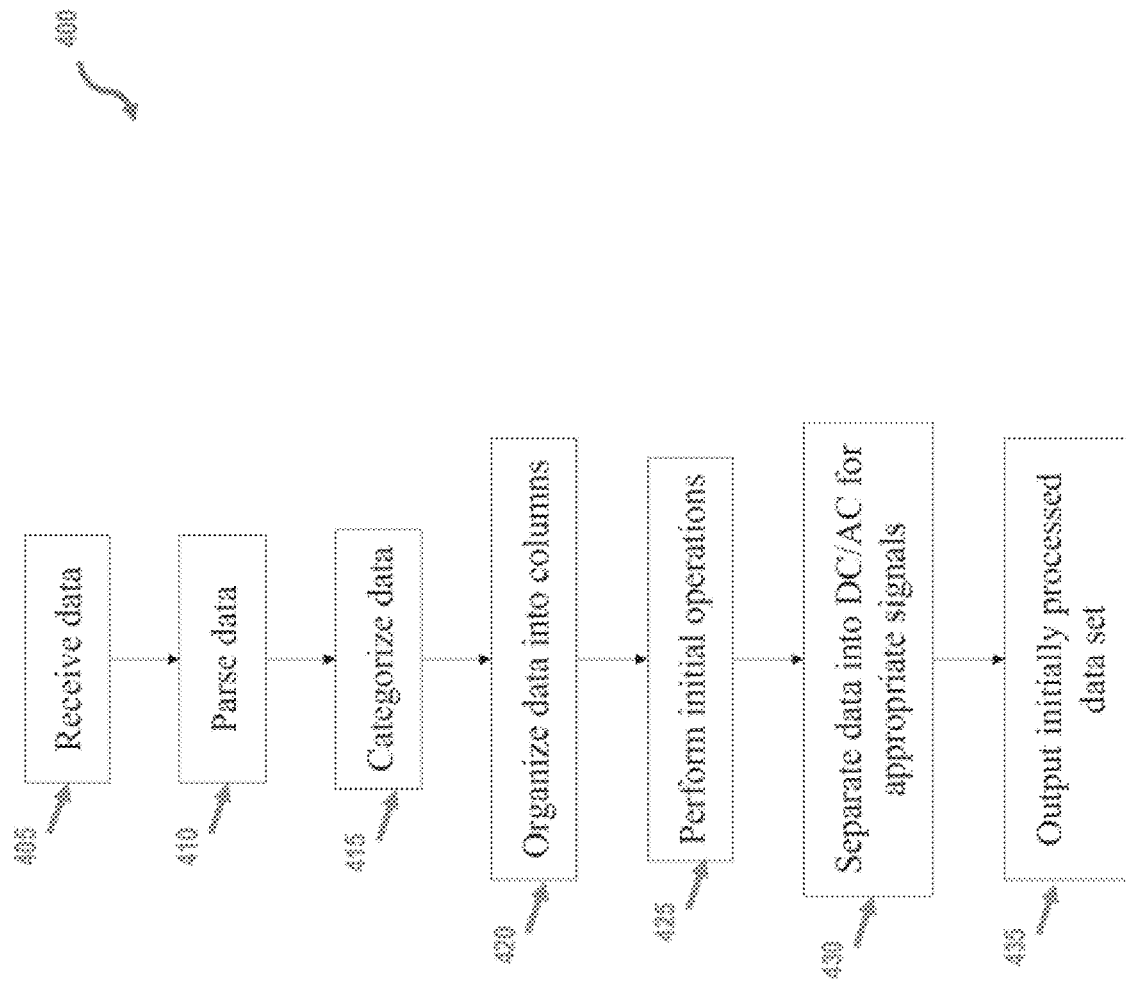
FIG. 4 is a flowchart describing a process for determining one or more signal-derived features/metrics according to various embodiments of the present disclosure.

FIG. 4 is a flowchart describing a process for determining one or more signal-derived features/metrics according to various embodiments of the present disclosure. In various embodiments, and as will be further discussed herein, data is received by the system, which then is transformed into a parameter with a timeseries (e.g., a series of data points that are indexed in time order).

The flowchart begins at block 405, where data is received. In one embodiment, the received data is the data from the patch device 100 used by the patient. In one embodiment, the system can extract the timeseries from a raw data file (e.g., received from the patch device 100). In various embodiments, the data is received from the plurality of sensors and may be in binary format. In one embodiment, the data from each sensor is received as its own binary file. One advantage to a central processor being used, as illustrated in FIG. 2, is that all of the data is being received at one central processor. This allows for all of the data to be received at one location and associated with the same set of time data (e.g., from the clock or a like component). Further, using a single processor may eliminate programming and hardware complexities as the single processor and collect and collate all sensor data into a single or multiple data files.

At block 410, the system parses the received data. In at least one embodiment, the system parses the received data into individual sensor data (e.g., if the sensor data is bulk data with data from multiple sensors in a single data file), into data based on time information (e.g., segments data into discrete time segments), and/or parses the received data into discrete information, such as, for example, separate red and IR data received from the PPG sensor.

At block 415, the system categorizes the data. In one or more embodiments, the system categorizes the data into different data types (e.g., PPG data, etc.) and/or column vectors discussed below in relation to block 420. In some embodiments, the system categorizes the data into DC and AC data (discussed below). In at least one embodiment, the system categorizes the data into noisy and clean data based on a preliminary analysis of the received data.

At block 420, the system organizes the data into a plurality of columns corresponding to the categories as determined at block 415. In one embodiment, the timeseries is stored in column vectors, which may correspond to: timestamps, three-axis accelerometer, IR, PPG, and ECG.

At block 425, initial operations are performed. In one embodiment, the system can precondition each timeseries to remove filler values, (e.g., values of −1 from the lower data rate PPG) and can resample the timeseries using the method of interpolation. Interpolation can include a process of upsampling a set of data and filtering the upsampled data. According to at least one embodiment, the system determines one or more Nyquist frequency for one or more signals. The system can use interpolation to generate timeseries to have sampling rates above twice the Nyquist frequency of the given signal. As an example, the system can utilize a sampling rate greater than twice the Nyquist frequency. The system can prevent aliasing by using a sampling rate above twice the Nyquist frequency. The system can down sample the interpolated timeseries to reduce file size. The system can reduce an process runtime by down sampling the interpolated timeseries. According to one embodiment, the following values are the constant sampling rates for resampling particular signals of respective sensors: Raw accelerometer @ 500 Hz (for seismocardiogram (SCG), phonocardiogram (PCG)), ECG @ 250 Hz, and PPG @ 50 Hz.

At block 430, the data is separated as either a pulsatile component (AC) or non-pulsatile component (DC), whichever may be appropriate. In various embodiments, the system separates data collected from various sensors (e.g., ECG, PPG, and accelerometer, etc.) into AC and DC components. In at least one embodiment, the DC component is a set of values that may contain a baseline wander and the AC component is a set of values that may exclude the baseline wander. In particular embodiments, baseline wander is a type of noise produced in various sensors, though primarily in an ECG sensor.

At block 435, the system outputs (or saves to memory) the initially processed data for further use, which will be discussed with reference to figures below.

Figure 5:
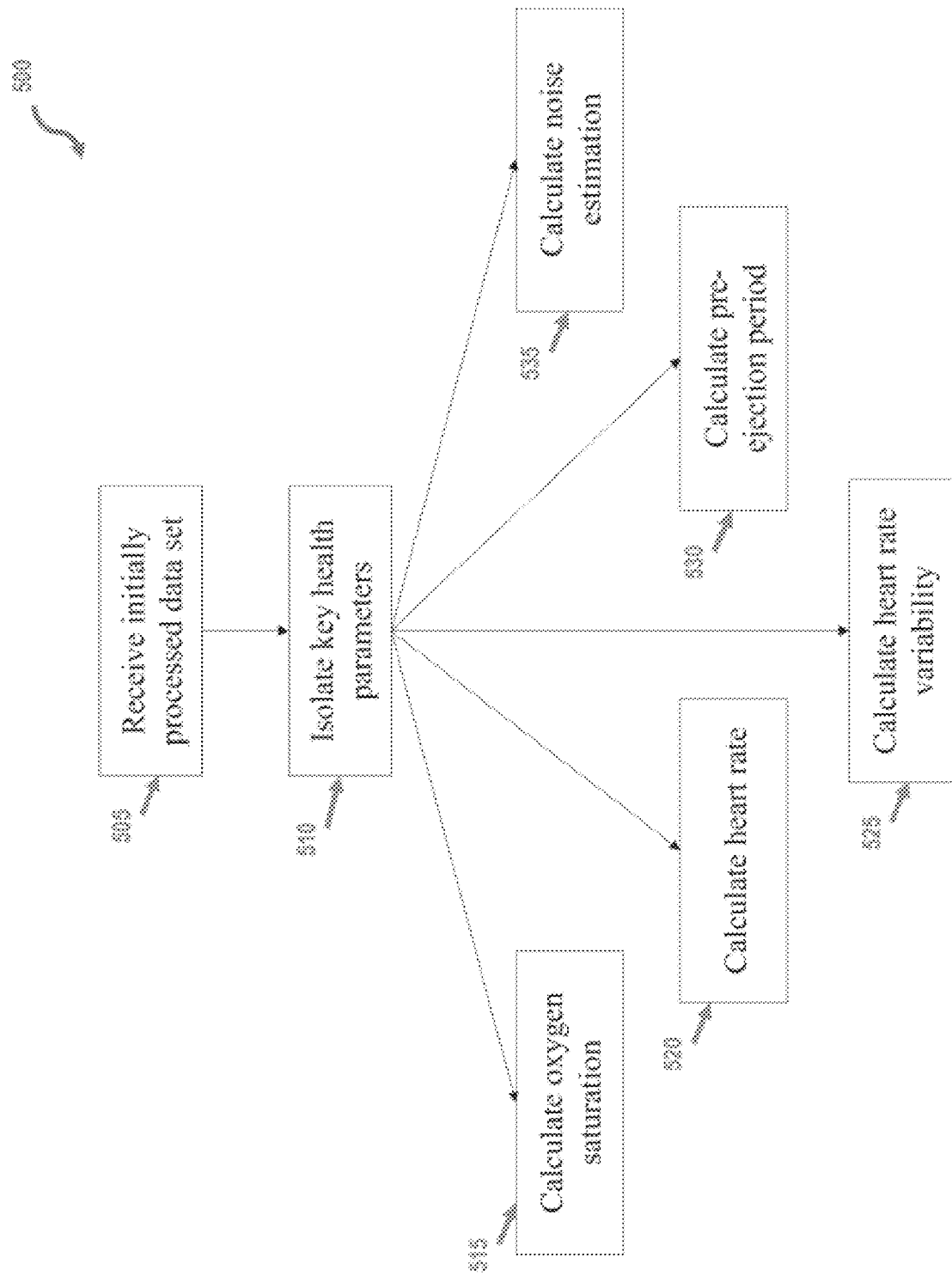
FIG. 5 is a flowchart illustrating the calculation of a variety of derived parameters according to various embodiments of the present disclosure.

FIG. 5 is a flowchart illustrating computation of a variety of derived parameters according to various embodiments of the present disclosure. Many parameters may be derived, including, but not limited to, oxygen saturation (SpO2), heart rate (HR), HRV, pre-ejection period (PEP), and noise estimation from the data collected by the sensors, including the PPG sensor (as discussed with reference to FIG. 1).

At block 505, the initially processed data set is received. In one embodiment, the initially processed data set corresponds to those processed and outputted at block 435 in FIG. 4.

At block 510, key health parameters are isolated. In one embodiment, the system can apply filters to the data to extract or isolate key health parameters. As an example, the system can apply a bandpass filter to a data signal to isolate a specific band of frequency for further processing. As an example, the system can digitally bandpass filter the AC content of both the red and IR PPG channels at a range usually around 0.5-6 Hz. The system can segment the filtered PPG data according to the R-peaks for subsequent analysis. The system can take the ratio of the AC signal with respect to the DC signal of each PPG channel. Taking this ratio can be referred to as taking the perfusion index. The flowchart then proceeds to at least one of blocks 515, 520, 525, 530, 535, and/or 540.

At block 515, the oxygen saturation content is calculated. In one embodiment, the system can calculate the SpO2 content in a variety of ways by using the processed PPG's AC and DC data. The system can employ the optical ratio (R) to calculate the SpO2 content. The optical ratio can be a ratio of ratios between the Red's AC and DC data and the IR's AC and DC data.

In one example, the following formula can illustrate an exemplary optical ratio:

$$R = \frac{AC_{rms\ RED} / DC_{rms\ RED}}{AC_{rms\ IR} / AC_{rms\ IR}}$$

Where the R can represent the optical ratio, ACrms RED can represent the root means square of AC data collected by red lights in the PPG, DCrms RED can represent the root means square of DC data collected by red lights in the PPG, ACrms IR can represent the root means square of AC data collected by IR lights in the PPG, and DCrms IR can represent the root means square of DC data collected by IR lights in the PPG. In some embodiments, other formulas for optical ratio may be utilized. The other formulas may be selected based on a lower error rate when compared to the above-referenced formula. The above-formula is included herein for exemplary purposes.

In one embodiment, the system can calculate the optical ratio by using one or more of the following methods. The least-square-optimized (LSQ) method can be used by calculate a value of R by minimizing the error shown in the following formula:

$$e = AC_{RED} - R \cdot AC_{IR}$$

Where e can represent the error, $AC_{RED}$ can represent the AC data collected by the red light in the PPG, and $AC_{IR}$ can represent the data collected by the IR light in the PPG. Other methods the system can use to calculate the optical ratio include beat-to-beat (B2B), exponentially weighted moving average (EWMA), beat-averaged (AVG), intervallic (INT), intervallic FFT, intervallic peak (PKS), and enveloped (ENV), etc. In some embodiments, the system can compute the optical ratio using multiple methods to verify, average, identify problems, or otherwise improve the optical ratio determination. The system can use a B2B method for calculating the optical ratio by taking the peak-to-peak amplitude ratios of the DC and pulsatile (AC) data, collected from the segmented PPG beat. The system can use a EWMA method for calculating the optical ratio by taking the B2B data and smoothening it with a weighted moving average filter and a forgetting factor of A (lambda)>0.75. The "forgetting factor" can refer to a value which gives exponentially less weight to older error samples. The system can use AVG as a method to calculate the optical ratio by using the same methodology as B2B, but applying that methodology to interval-averaged PPG beats (e.g., the ensemble average of all PPG beats with a certain time window). The system can use INT as a method to calculate the optical ratio by defining the AC and DC values across a given time window segment of the PPG data (instead of beat-to-beat). The system can apply an FFT to segmented time intervals of the raw PPG signal, and each segment's spectrum can be used to define the AC and DC content of the PPG channel, with the AC amplitude corresponding to the maximum peak in the cardiac frequency band (e.g., between 0.5 and 2.5 Hz). The system can use PKS as a method for calculating the optical ratio by detecting peaks from red and IR pulses in a given window and calculating the ratios of the peaks from red and IR pulses. These ratios can be average for a given time interval. The system can use ENV as a method for calculating the optical ratio by defining the pulsatile (AC) amplitude for a given interval. This AC value can be calculated using an envelope constructed by a rolling window maximum operation. Envelopes in this context may be used as a method for calculating the optical ratio by defining the pulsatile amplitude for a given interval.

At block 520, heart rate is calculated. In one embodiment, the system can compute beat-to-beat HR from the R-R intervals, such as, for example, by subtracting the time between two successive R-peak intervals.

At block 525, heart rate variability is calculated. In one embodiment, the system can calculate HRV using the R-R interval values. The system can use time-domain approaches, frequency-domain approaches, and/or nonlinear approaches to calculate HRV. For time-domain approaches, the system can use root means square of successive differences (RMSSD) and the standard deviation of NN intervals (SDNN). RMSSD can include taking the root mean square of successive differences between consecutive R-peaks. SDNN can include taking the standard deviation between two consecutive normal R-peaks. The frequency-domain approach can include using the ratio between the low frequency (LF) and the high frequency (HF) values. For a nonlinear approach, the system can calculate HRV using Poincare plots, a method that can be used to detect the presence of oscillations in non-linear systems. In various embodiments, the system can vary the window size of the R-R interval time series data for calculating HRV from ~20 seconds to ~20 minutes or more to record respiratory events and sleep staging, respectively. The system can segment ECG beats according to R-peak values and store this data in a beat array for subsequent analysis.

At block 530, a pre-ejection period is calculated. The PEP may correspond to the delay between the R-peak and the AO point. In one embodiment, the PEP values are plotted on a graph. This graph can show the points at which an apnea event terminates for a user with obstructive sleep apnea. The increase in heart rate can cause an increase in cardiac inotropy, which can shorten the PEP. These measurements can also be displayed on the PEP graph. On such a graph, the PEP measurements dip at apnea termination (e.g., at the end of the respiratory disturbance), as shown by the arrows.

At block 535, noise estimation is calculated. In one embodiment, the system can be used to assess or determine peaks per beat. A classical PPG beat contains at most two discernable local maxima (one for the forward-traveling pulse wave, and one for the reflected wave). The system can flag a beat that contains three or more detectable peaks as potentially corrupted by artifacts based on the definition of classical PPG described previously herein. For the system, a time window that exceeds a certain number of "outlier" peaks (e.g., a configurable threshold number) can be considered noisy. The system can determine that a time window with a peak amplitude variance (e.g., peak heights modulating chaotically and drastically beat to beat) that meets or exceeds the threshold is noisy.

Figure 6:
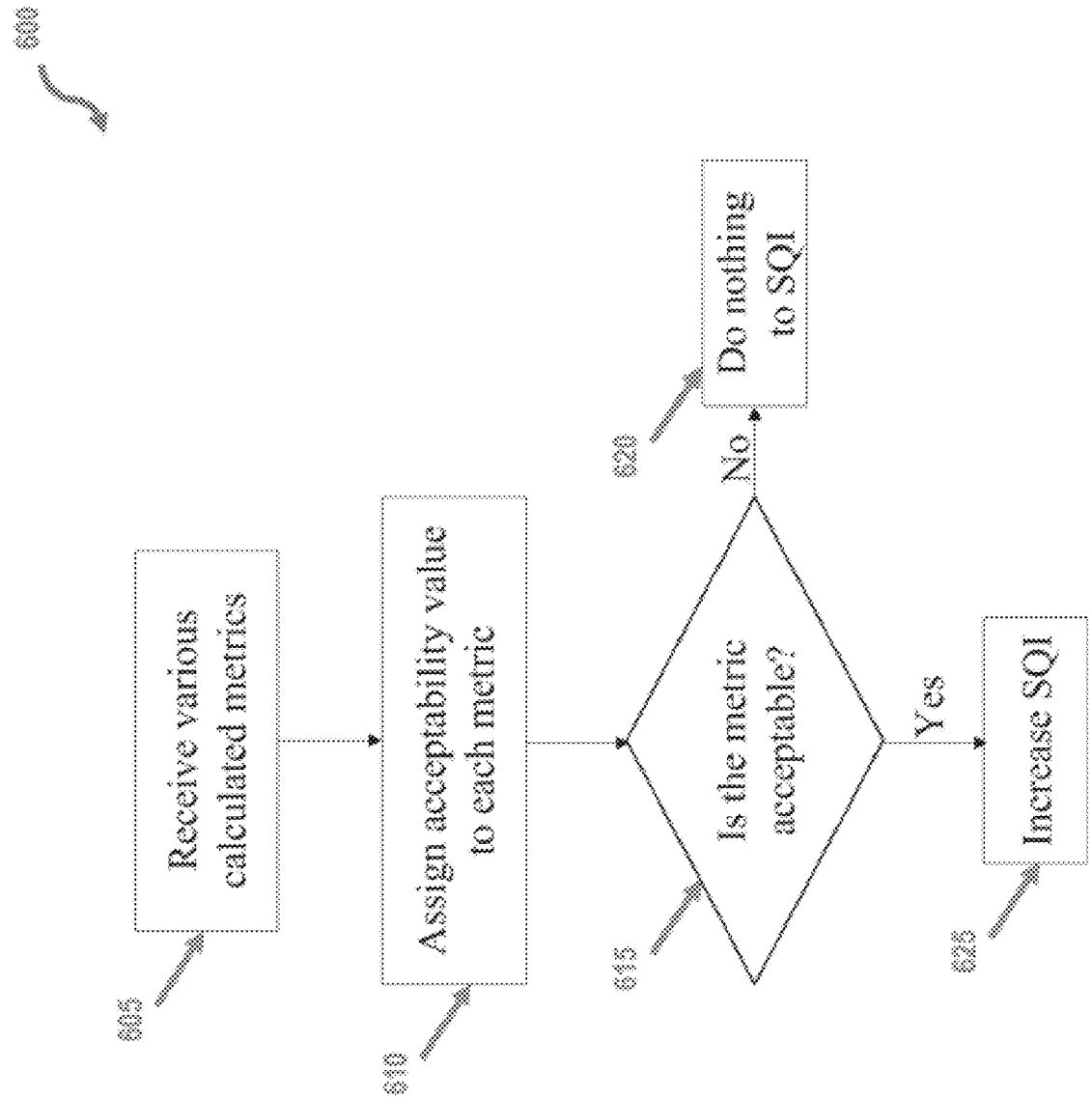
FIG. 6 is a flowchart describing the process to calculate signal quality index (SQI) according to various embodiments of the present disclosure.

FIG. 6 is a flowchart describing the process to calculate signal quality index (SQI) according to various embodiments of the present disclosure. In one embodiment, the system can combine various metrics to compute a composite SQI. These various metrics may include any of the variety of metrics previously discussed.

In one embodiment, the data collected by the PPG sensor can be compared with data collected by the ECG sensor to verify the accuracy of the data. In another embodiment, a multitude of other sensors can capture and determine a same vital statistic (e.g., a heart rate) such that if a particular sensor reads incorrect data (e.g., because the particular sensor shifted, was pushed, was bumped, encountered sweat or water, etc.), the measured vital statistic from another one of the other sensors can be used instead until the particular sensor is fixed or reads correctly. In one embodiment, the system removes the incorrect data, rather than the system fixing the sensors, which can be done as a step with computing the composite SQI.

The process begins at block 605 where a plurality of metrics are received. In one embodiment, the metrics may correspond to cardiodicity, red-IR cross-correlation, local distance, local variance, and/or pulse amplitude.

Then, at block 610, the metrics are given an "acceptability" value. Said another way, each individual quality metric may be assigned an "acceptable" threshold value (e.g., a predetermined threshold value, depending on the parameter).

At block 615, the system determines if the metric is acceptable based on the predetermined threshold value. If it is not acceptable, the method proceeds to block 620, and the SQI remains unchanged. If the metric is acceptable, the method proceeds to block 625 where the SQI is increased. In one embodiment, if the metric falls on the "accept" side of the threshold, the system can give a weighted "vote" toward the SQI. The system can then calculate the SQI as a weighted sum of all signal quality metrics' votes. The system may use this composite average of individual, orthogonal quality metrics calculated on a window-by-window basis such that it can be expressed as a timeseries and used to reject certain regions of interest within each record that do not meet a predefined SQI threshold.

The system can calculate the SQI for PPG in various ways. Template matching is the process of matching small parts or portions of a signal to a template signal. A good-quality PPG may generally appear stable and consistent in morphology at relatively short timescales. Morphology may include the study and description of geometrical images or signals. The system can capture this behavior quantitatively by comparing individual PPG beats to a template, which can be defined as the ensemble average beat in a given time window sized, for example, to contain at least 5 beats, at least 10 beats, at least 15 beats, or some other size. The system can do this to ensure "consensus" when averaging. The system may quantify the beat-to-beat variance by calculating the standard deviation around the local ensemble average ("local variance"). The system can also capture local signal consistency measurements by computing the "distance" between the individual beat and its local template ("local distance"). The system can determine "distance" by computing via dynamic time warping, cross-correlation, cosine similarity, coherence, or any other metric that compares two or more signals. For a peak-to-peak pulsatile amplitude, the system can extract the AC amplitude on a beat-to-beat basis. In various embodiments, if the system records high pulse amplitudes, this can correspond to a high signal-to-noise ratio (SNR) PPG.

The system can be used to assess or determine peaks per beat. A classical PPG beat contains at most two discernable local maxima (one for the forward-traveling pulse wave, and one for the reflected wave). The system can flag a beat that contains 3 or more detectable peaks as potentially corrupted by artifacts based on the definition of classical PPG described previously herein. For the system, a time window that exceeds a certain number of "outlier" peaks (e.g., a configurable threshold number) can be considered noisy. The system can determine that a time window with a peak amplitude variance (e.g., peak heights modulating chaotically and drastically beat to beat) that meets or exceeds the threshold is noisy.

A high-quality PPG signal can contain physiologically expected information (e.g., signal in the cardiac frequency band) and little else otherwise (e.g. artifact). For the system to determine the strength of the cardiac component of the PPG, it can segment the time windows, containing at least 5 beats, and can compute a normalized autocorrelation for each window. The term "cardiodicity" (periodicity at the dominant cardiac frequency) refers to the highest autocorrelation peak in the cardiac band (0.5-2.5 Hz), if one exists.

The system can use a red and IR LED along with a sensor to measure PPG over the desired tissue area. In various embodiments, the system may illuminate the same location with both LED's, which can illuminate the same volume of blood during each pulse. The system can consider this and determine that the cross-correlation between each channel may be high (ideally=1), and use this information to treat disparities between channels as the consequence of artifacts.

The ideal PPG signal can be characterized by high pulsatile amplitude, high perfusion index, low noise, high beat-wise repeatability, low beat-wise variance, and high cardiac frequency content. The system can combine the previously describe metrics to compute a composite signal quality index (SQI). For the system to calculate SQI, each individual quality metric (e.g., cardiodicity, red-IR cross-correlation, local distance, local variance, pulse amplitude) may be assigned an "acceptable" threshold value. As stated above, if the metric falls on the "accept" side of the threshold, the system can give a weighted "vote" toward the SQI. The system can then calculate the SQI as a weighted sum of all signal quality metrics' votes. The system may use this composite average of individual, orthogonal quality metrics calculated on a window-by-window basis such that it can be expressed as a timeseries and used to reject certain regions of interest within each record that do not meet a predefined SQI threshold. In other words, if the metrics are given an acceptable value at two instances, it is known that the metrics are high quality. If the metrics are only given one acceptable value, the metrics should be tested again and calculated for acceptability. If the metrics do not meet an acceptable threshold, the metrics should not be used. In one embodiment, the quality and fidelity of the calculated SpO2 are indexed by computing a normalized cross-correlation or Pearson's correlation coefficient between pulsatile red and IR signals within a time window of up to 10 seconds in length.

The system can calculate the SQI for SCG in the same or similar way that the SQI is computed for the PPG, except with only a subset of signal quality metrics getting a vote (e.g., peak-to-peak amplitude, local distance, local variance, cardiodicity). The system can calculate the SQI for ECG in the same way SQI is computed for the PPG, except with only a subset of signal quality metrics getting a vote (e.g., peak-to-peak amplitude, local distance, local variance, cardiodicity).

Figure 7:
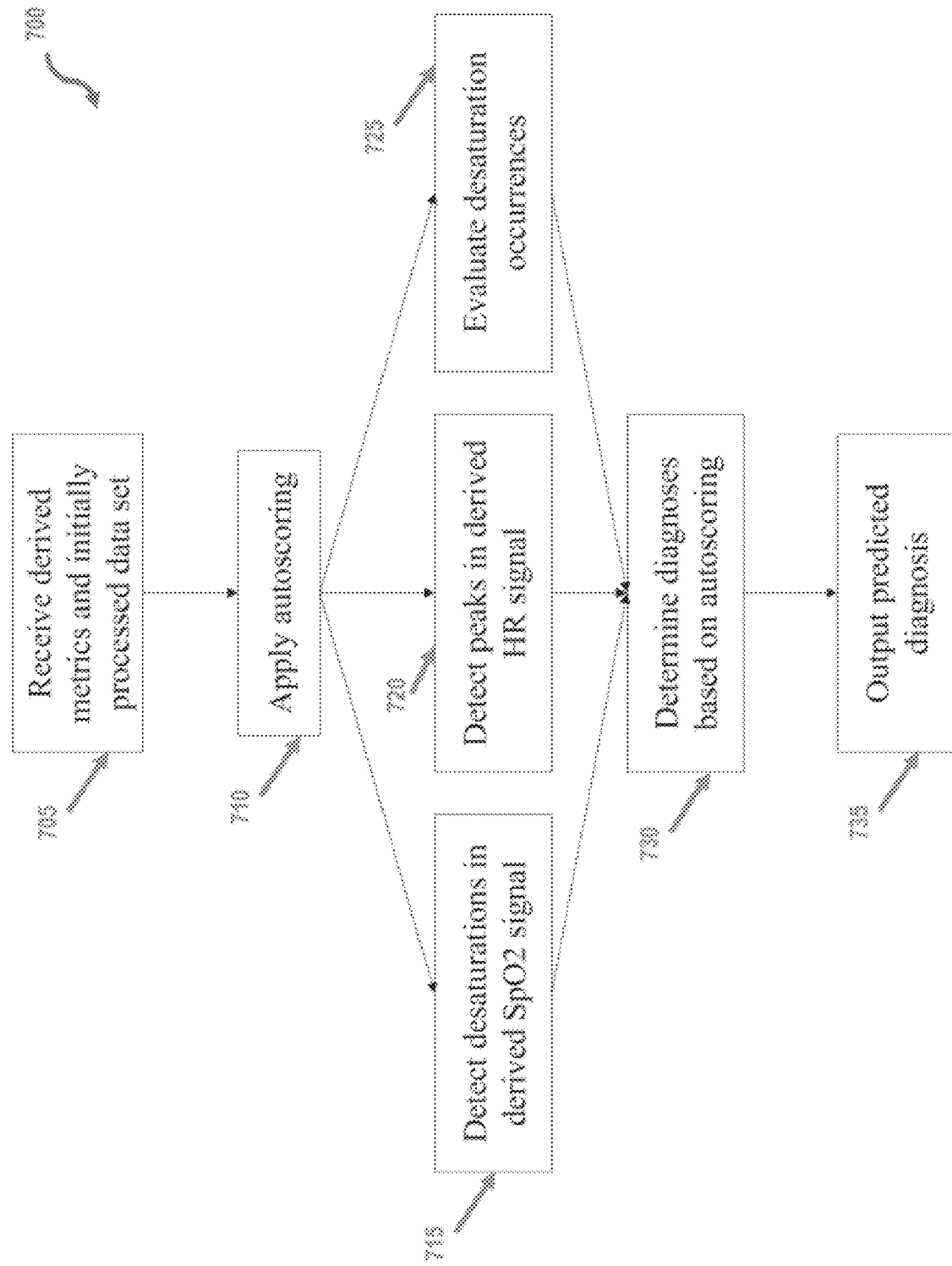
FIG. 7 is a flowchart describing the process to use autoscoring to predict a diagnosis according to various embodiments of the present disclosure.

FIG. 7 is a flowchart describing the process to use autoscoring to predict a diagnosis according to various embodiments of the present disclosure. The flowchart begins at block 705 where derived metrics and the initially processed data set are received. In one embodiment, the derived metrics are those that were created at block 415 in FIG. 4, and the initially processed data set is that which was outputted at block 435 in FIG. 4.

At block 710, the system receives data for autoscoring. In one or more embodiments, the system's autoscore, which is the method by which the system can detect respiratory disturbances like apneas and hypopneas automatically from derived parameters like HR, SpO2, etc., can be influenced by various scoring guidelines, such as, for example, the American Academy of Sleep Medicine (AASM) scoring guidelines. The autoscore can represent a baseline attempt that leverages a limited number of signals that could be utilized by a sleep technician scoring a sleep study. The system may incorporate more sophisticated methodologies, such as machine learning, for autoscoring.

The system can detect changes from baseline in given physiological signal. The system can determine if changes meet a threshold difference and threshold duration that would qualify it as event-worthy. Moreover, the system can determine if event-worthy changes in the defined parameters occur in the proper order and proximity in time relative to one another. The system can sum the valid event-worthy responses in multiple signals to form an event likelihood index.

One common series of physiological phenomena occurs during the incidence of a sleep disordered breathing event: (1) a decrease in respiratory effort, (2) a decrease in blood oxygenation, (3) an arousal from sleep, which may follow one another in numerical order. In some embodiments, the system can detect three physiological time series derived during a feature extraction to represent the following three phenomena: (1) respiratory effort from low-frequency accelerometry, (2) SpO2 calculated from red/IR PPG, and (3) heart rate calculated from ECG. The system can detect decreases in respiratory effort as a trough in the amplitude envelope of the respiratory accelerometer signal. The amplitude envelope is a representation of the change in a sound's energy over time, which is detected from the heart sounds. The mediolateral axis of the accelerometer can provide the most sensitive measurement of respiratory effort relative to a standard RIP belt, though any combination of the three axes by the system can be used. In one embodiment, the processor of the patch device 100 can compute a Euclidean distance of the three-axis accelerometer sample-by-sample. The Euclidean distance can be used to calculate a distance between each point of the three-axis accelerometer to determine a three-dimensional distance between various locations. More specifically, the system can determine the distance between data points in a three-dimensional plane. The device can arrange the SCG, PCG, and KCG data using R-peaks of individual heartbeats and store these values into beat arrays for subsequent analysis.

To ensure even minor contractions of the respiratory effort may be considered, the system can capture envelopes (since respiratory effort may remain relatively high even during obstructed breathing) and trough detection threshold can be set at a conservative value (normally ~80% of the local baseline value). The system can detect troughs with minimal spacing in between (10 seconds), consistent with AASM guidelines that airway obstructions manifest for at least 10 seconds for it to be considered an apnea or hypopnea. The system can exclude segments based on SCG or ECG SQI if respiratory effort appear highly chaotic due to motion artifacts. Additionally, in various embodiments, the detection of a respiratory disturbance is gated by sleep stage as determined by a combination of information regarding motion and cardiovascular state. In some embodiments, the information regarding cardiovascular state comprises time- and frequency-domain features of heart rate computed in windows of length 30 seconds or greater, and the windowed features are used as inputs to a supervised machine learning model which renders time-varying sleep stage (wake, REM, non-REM) estimations in windows of length 30 seconds or greater.

At block 715, the system can detect desaturations as troughs in the derived SpO2 signal. Desaturations can imply the number of times the oxygen level in the blood drops below baseline. The system may ensure the SpO2 nadirs (e.g., the lowest oxygen saturation values a particular patient drops to) have a prominence of 3% (or some other threshold) or greater to qualify as an event (4% depending on the insurance provider), which can be consistent with AASM scoring guidelines. The system can require that the SpO2 nadirs be spaced at least 10 seconds apart to avoid overdetection of spurious troughs. The system can correct SpO2 signals by subtracting baseline wander if the baseline shifts in SpO2 are apparent and problematic (such as can be the case when a subject changes positions). If SpO2 appears highly chaotic due to poor PPG signal quality, the system can exclude segments based on PPG SQI, and/or multiple SpO2 processes can be averaged together to form a "consensus" SpO2.

At block 720, the system detects arousals as peaks in the HR signal (e.g. tachycardia). For tachycardia to be considered, the system can ensure a deviation by 3 beats per minute (BPM) or greater is detected from the baseline HR. In some embodiments, the system can detect HR peaks as long as the peaks are at least 10 seconds apart. The system can exclude segments based on ECG SQI if HR appears highly chaotic due to motion artifact.

At block 725, the system evaluates desaturation occurrences. In one embodiment, the system can scrutinize all respiratory contractions, desaturations, and tachycardia's to see if they occur in the predetermined sequence. The system can mark a desaturation occurrence as a valid effort-desaturation dyad if the desaturation occurs within a predetermined timeframe after a respiratory contraction. The system can mark a tachycardia occurrence as a valid desaturation-arousal dyad if it occurs within a certain timeframe after a desaturation. If the system can detect that both dyads happened in sequence, it is deemed a valid event triad and is tallied as a respiratory disturbance (which can be used for either an apnea or a hypopnea). If the system can detect that only one dyad occurred, the system can label the sequence as a possible respiratory disturbance (with a likelihood percentage computed and assigned based on the SQI of each contributing signal).

At block 730, the system determines a predicted diagnosis based on autoscoring. In one embodiment, the autoscoring may provide an indication of what particular diagnosis may be applicable based on the patent data and metrics described above. For example, if the derived metrics that have been autoscored show an abnormal breathing pattern, then a predicted diagnosis may be of sleep apnea.

At block 735, the system outputs the predicted diagnosis. In one embodiment, this predicted diagnosis may be used by a physician to provide a patient with medications or therapies that may remedy or repair the diagnosis. In various embodiments, the predicted diagnosis may be out to a display, notification (including, for example, text message, email, system notification, portal notification, portal message), or the like. In at least one embodiment, the system may be configured to modify at least one display to display or otherwise convey the predicted diagnosis.

Figure 8:
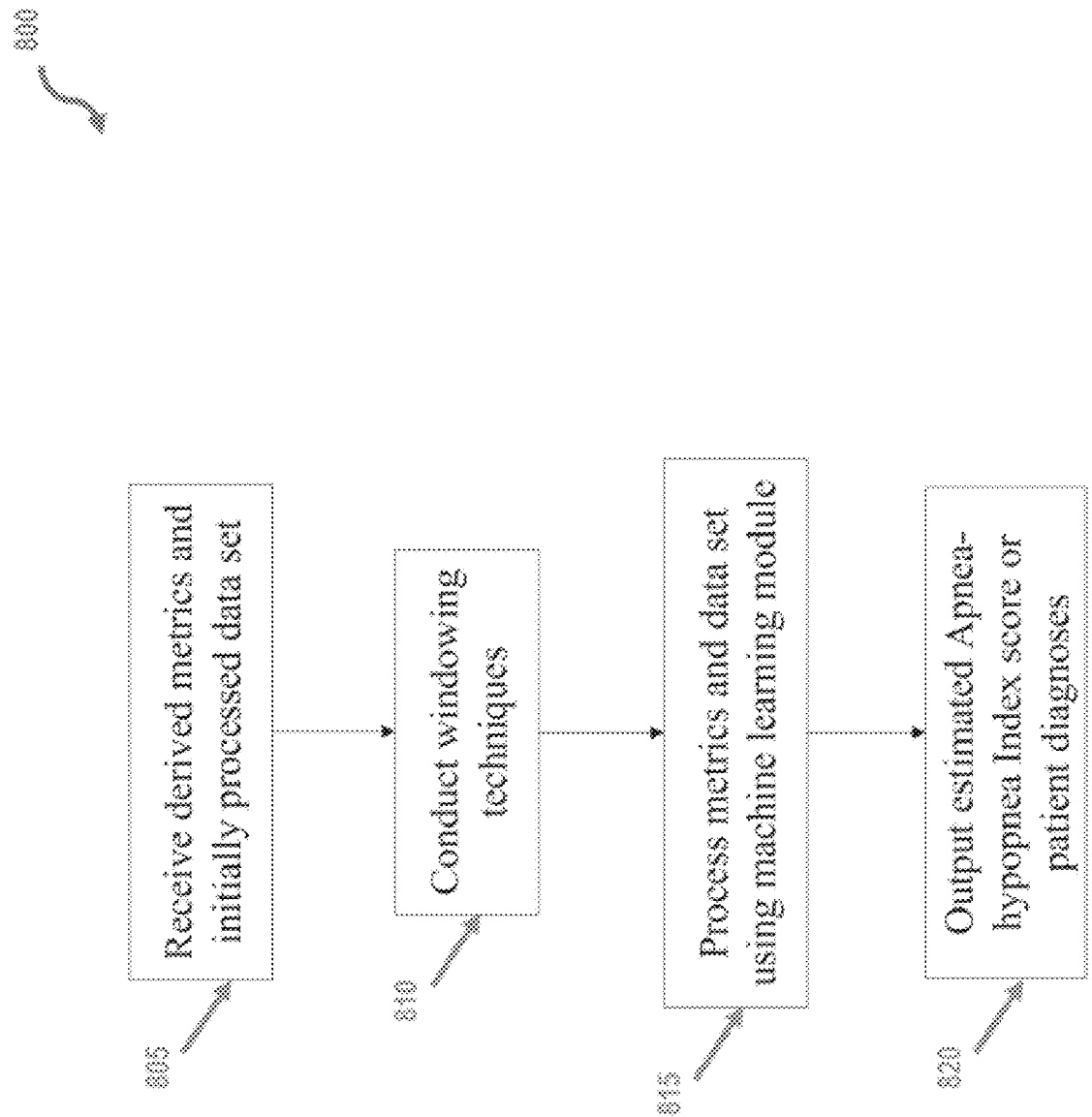
FIG. 8 is a flowchart showing an exemplary machine learning process according to various embodiments of the present disclosure.

FIG. 8 is a flowchart showing an exemplary machine learning process according to various embodiments of the present disclosure. The flowchart begins at block 805 where derived metrics and the initially processed data set are received. In one embodiment, the derived metrics are those that were created at block 415 in FIG. 4 and the initially processed data set is that which was output at block 435 in FIG. 4.

At block 810, windowing techniques are applied to the metrics and data set. A window may be adjusted using a variety of different techniques to create different metrics. According to at least one embodiment, window functionality comprises three steps: detection of an overlap between a plurality of windows, application of operations to each of the windows, and development of a windowed feature time series. The operations that may be applied vary and are discussed in the following paragraphs.

In one embodiment, periodicity in a respiration band is calculated. Normalized autocorrelation is applied to the windows. This is done to detect in-band peaks. In another embodiment, peak orderliness or predictable amplitude modulation is calculated. Peaks on the developed graphs are detected. For example, hypopnea or respiratory decoupling of PPG may be detected at these peaks. A polynomial fit (e.g., (y=mx+b), (y=mx$^2$+bx+c)) is then applied to these graphs with detected peaks. From there, a goodness-of-fit (R$^2$/RMSE) calculation is made.

In yet another embodiment, signal stochasticity is calculated. Initially, activity is calculated at each window: var(x). The mobility is then calculated: the square root of (var(x')/activity. Finally, the complexity is calculated: the square root of (var(x")/var(x'))/mobility. According to at least one embodiment. The dominance of suitable frequency is detected, otherwise called fast Fourier transform (FFT) peakedness. Initially, the FFT peak is calculating using a plot. The crest factor is then calculated by taking $P_{MAX}$ divided by $P_{RMS}$.

According to at least one embodiment, the system can create a DC data set by using a moving average filter of a particular window size (e.g., approximately between 5-30 seconds). The system can apply the moving average filter (e.g., to a time domain signal) to reduce short term fluctuations and accentuate long term patterns. The AC component can include all the data that was not filtered out by the moving average filter.

In various embodiments, the system can vary the window size of the R-R interval time series data for calculating heart rate variability (HRV) from ~20 seconds to ~20 minutes or more to record respiratory events and sleep staging, respectively. The system can apply a moving-window (e.g., interval-based) ensemble averaging to the beat arrays constructed for the ECG, red PPG, IR PPG, SCG, PCG, and KCG. As an example, the system can calculate the moving window ensemble average to the beat arrays.

At block 815, the metrics and data set are processed using a machine learning module. In one embodiment, the machine learning module is machine learning module 320 in FIG. 3. In one embodiment, machine learning is used for autoscoring. In particular embodiments, the first step in the construction of a "grey box" machine learning (ML) based autoscore for detecting sleep disordered breathing events and estimating an Apnea-hypopnea Index (AHI) is to generate a set of features to serve as inputs (predictors) to the process. In one or more embodiments, the term "grey box" refers to the limited, but in some cases non-zero, ability to change various aspects of the machine learning system. In various embodiments, to make the model more interpretable to a clinical audience, the process is grounded in physiologically relevant features derived from each of the time-series signals collected by the system. Input features for the ML autoscore may derive from time-series signals (e.g., ECG, PPG, SCG, PCG) and derived parameters (e.g., SpO2, HR, HRV, PEP, noise estimation). These time-series feature substrates may include, but are not limited to:

PPG
  Red and IR
  Raw, AC, DC, and digitally filtered
ECG
  Raw, AC, DC, and digitally filtered
Raw accelerometer
  x-, y-, and z-axes
Respiratory effort
  x-, y-, and z-axes
Respiratory rate
Body position
SCG
  x-, y-, and z-axes
  Euclidean norm
  Amplitude-enveloped
PCG
  x-, y-, and z-axes
  Euclidean norm
  Amplitude-enveloped
HR
  HRV
  RMSSD
  SDNN
  LF/HF ratio
  Poincare plot dimensions
SpO2
  All methods as described previously (B2B, EWMA, FFT, ENV, LSQ, INT, PKS)
SCG fiducial point-based metrics (both beat-by-beat and locally averaged)
  Pre-ejection period (PEP)
  Left ventricular ejection time (L VET)
  Isovolumetric contraction time (ICT)
  Isovolumetric relaxation time (IR T)
  Diastolic filling time (DFT)
  Aortic opening (AO) amplitude
  Isovolumetric contraction point (ICP) amplitude
  Isovolumetric relaxation point (IRP) amplitude
  Systolic peak complex energy
  Diastolic peak complex energy
PCG fiducial point-based metrics (both beat-by-beat and locally averaged)
  First heart sound (S1) amplitude
  S1 delay
  Second heart sound (S2) amplitude
  S2 delay
  S1/S2 amplitude ratio
  S1/S2 interval
PPG-based metrics (both beat-by-beat and locally averaged)
  Pulse arrival time (PAT)
  Pulse transit time (PTT) (PAT from PPG minus PEP from SCG)
  Reflection index
  Augmentation index
  Pulse amplitude
  Perfusion index
  2nd-derivative PPG (SDPPG) local optima
  Point of maximal acceleration (PMA)
KCG-based metrics (both beat-by-beat and locally averaged)
  Linear kinetic energy
  Linear force
Signal quality metrics
  Local distance of PPG, ECG, and SCG
  Local autocorrelation of PPG, ECG, and SCG
  Red-IR PPG cross-correlation
  PPG cardiodicity
  Composite signal quality index (SQI) of PPG, ECG, and SCG
Output metrics (labels)
  Manual scores from registered sleep technician, primarily the union of
    Central apnea
    Obstructive apnea
    Mixed apnea
    Hypopnea At block 820, an estimated API score or patient diagnoses are outputted. These outputs can provide a physician with an understanding of the patient's condition and advise on the diagnosis to further remedy any issues.

The present disclosure is directed to optimizing the detection of a patient's heartbeats, which may be useful in the estimation of the patient's SpO2. As discussed herein, current systems may collect noisy PPG data when placed on a patient's chest (or elsewhere on a patient) due to patient motion, breathing, snoring, etc. This noise may result in false PPG peaks or the like. The present systems and processes utilize novel hardware arrangements and signal processing to overcome some of these hurdles.

As will be understood from discussions herein, the techniques used throughout this disclosure may be used together. For example, and without limitation, the processes shown in FIGS. 9-11 may be used in conjunction with and/or to improve processes discussed in relation to FIGS. 1-8.

In various embodiments, the system may compare PPG sensor data and secondary data. The system may detect possible heartbeats in the PPG data, and compare that data with secondary data (e.g., data from electrocardiograms (ECG), bioimpedance, accelerometers, PPG sensors). When the secondary data is data from a PPG sensor, that data may be collected from a PPG sensor placed on a patient's finger, when such patient's pulse transit time is known. Using the primary data from the PPG sensor and comparing that data with secondary data (from any number of sources), the system may determine the patient's heartbeats. For example, the system may "line up" data (based on time) from a first data stream with data from a second data stream in order to determine whether the patient's heartbeats are detected.

According to various embodiments, the system may synchronize data streams associated with the PPG sensor data and the secondary data. The system may proceed to comparing the data streams and identifying which data points are associated with the patient's heartbeats, which may be used as the "verified" heartbeats. The system may proceed to determining the SpO2. The determination may be achieved by using the PPG data that is associated with the "verified" heartbeats.

The ECG sensors may detect heartbeats associated with the patient using voltage changes collected by the ECG sensors. This voltage change data may be time stamped. The PPG sensor data may detect the patient's heart rate. Using this heart rate data in connection with the ECG sensor data, the system may calculate the patient's SpO2. As one example, an adaptive filter may extract beat-to-beat heartbeats from a data signal corresponding to the PPG sensor and/or the ECG sensor, as described herein.

Figure 10:
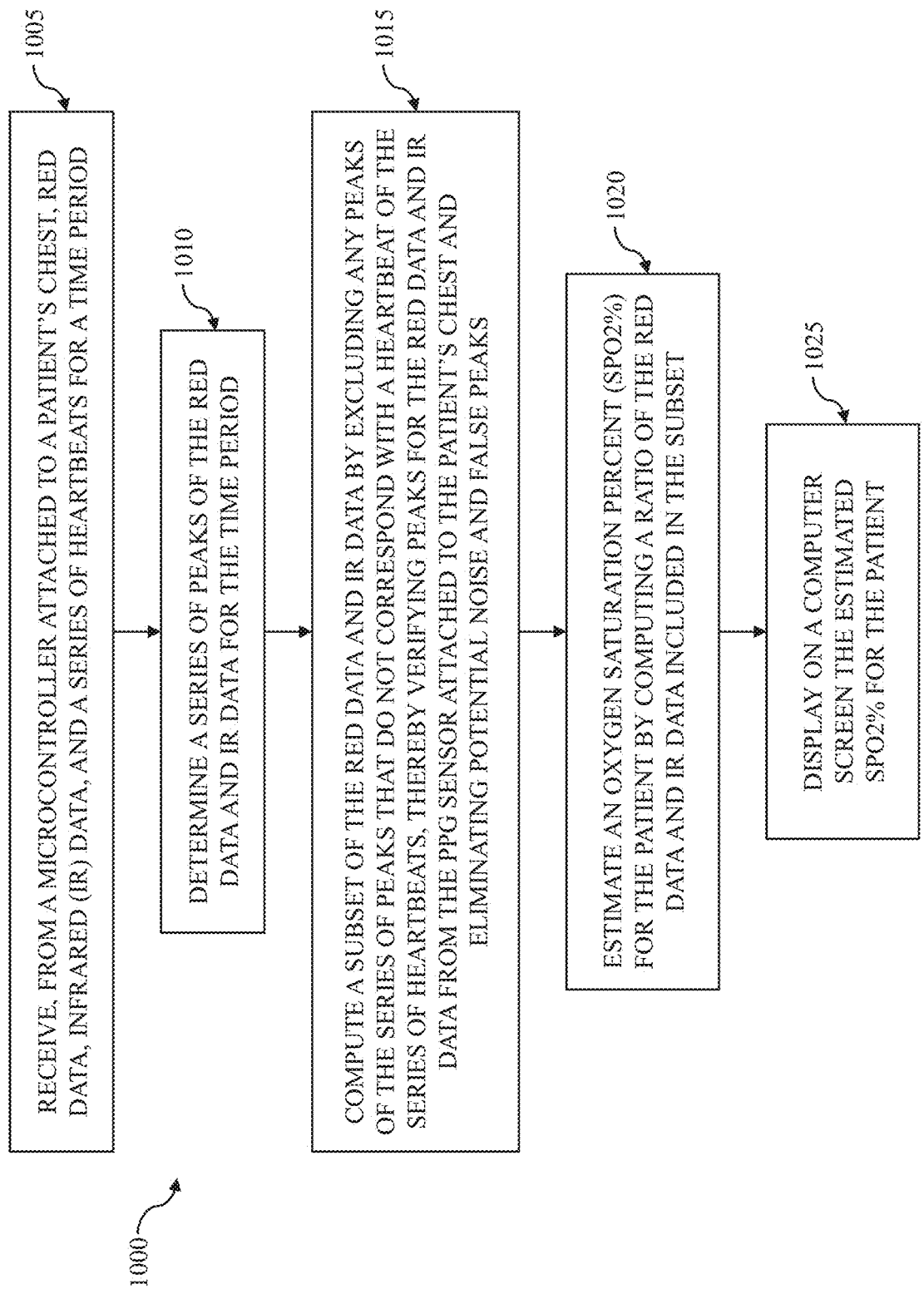
FIG. 10 illustrates a second flow chart of a second process according to various embodiments of the present disclosure.

According to various embodiments, and as will be further discussed herein, data may be received by the system, and such data may be transformed into a parameter with a timeseries (e.g., a series of data points that are indexed in time order). In one embodiment, the data from each sensor (e.g., PPG, ECG, bioimpedance, accelerometers sensors) is received by the system as its own binary file. One advantage to a central processor being used, as illustrated in FIG. 10, is that all of the data is being received at one central processor. This allows for all of the data to be received at one location and associated with the same set of time data (e.g., from the clock or a like component). Further, using a single processor may eliminate programming and hardware complexities as the single processor and collect and collate all sensor data into a single or multiple data files.

In various embodiments, the system may detect a possible heartbeat at a particular time. The system may then detect a window associated with that particular time for the ECG or other sensor data. The system may analyze whether that window is associated with the patient's heartbeat. The system may determine whether there are a series of data points associated with heartbeats, and if so, then the system may utilize such series to detect, with a reasonable degree of certainty, what data is associated with the patient's heartbeats. This data may include red and IR data, and that data may be filtered into AC and DC signals. Baseline wander may be analyzed in the ECG data. Other metrics may be analyzed in the PPG data, including pulse arrival time (PAT) and pulse transit time (PTT). PTT may be calculated by subtracting the pre-ejection period (PEP) associated with the SCG data from the PAT associated with the PPG data. These metrics may be analyzed on a beat-by-beat basis or may be analyzed as a local average.

Generally, in particular embodiments, systems and processes herein: 1) receive PPG data from a PPG sensor, including red data and IR data; 2) receive heartbeat data from a second sensor, sometimes referred to herein as a heartbeat detector; and 3) compare peaks of the PPG data with the heartbeat data from the second sensor (at a specific point in time or within a window of time) to confirm the peaks of the PPG data are associated with pulsatile component of blood flow, not noise or other data. As will be understood from discussions herein, accurate PPG data representing pulsatile blood flow can be important for accurate SpO2 estimations.

As will also be understood, in some embodiments, the system may be configured to compare PPG data and heartbeat data from the same time or related to the same physiological activity, which may be used to develop meaningful data. In various embodiments, the PPG sensor and the heartbeat detector may be included on a patch affixed to or worn by a patient and may be connected to a processor which is located on the patch. In these embodiments (and others), the processor may use the same clock or more than one clock to assign time data to the PPG data and the heartbeat detector data. In particular embodiments, the time data from one or more clocks may be synchronized by methods known in the art. In at least one embodiment, the system may leverage clocks from more than one processor and may synchronize data from the more than one clocks at a server (or other processor) using methods known in the art.

According to one or more embodiments, the heartbeat detector may be connected to the patient, but instead of being part of a patch that includes the PPG sensor, the heartbeat detector may be part of a separate device. In one such embodiment, a second PPG sensor attached to the patient (e.g., on a patient's finger, forehead, etc.) may serve as a heartbeat detector, and the system may synchronize data from the PPG sensor and data from the second PPG sensor using a pulse transit time of the patient.

Figure 9:
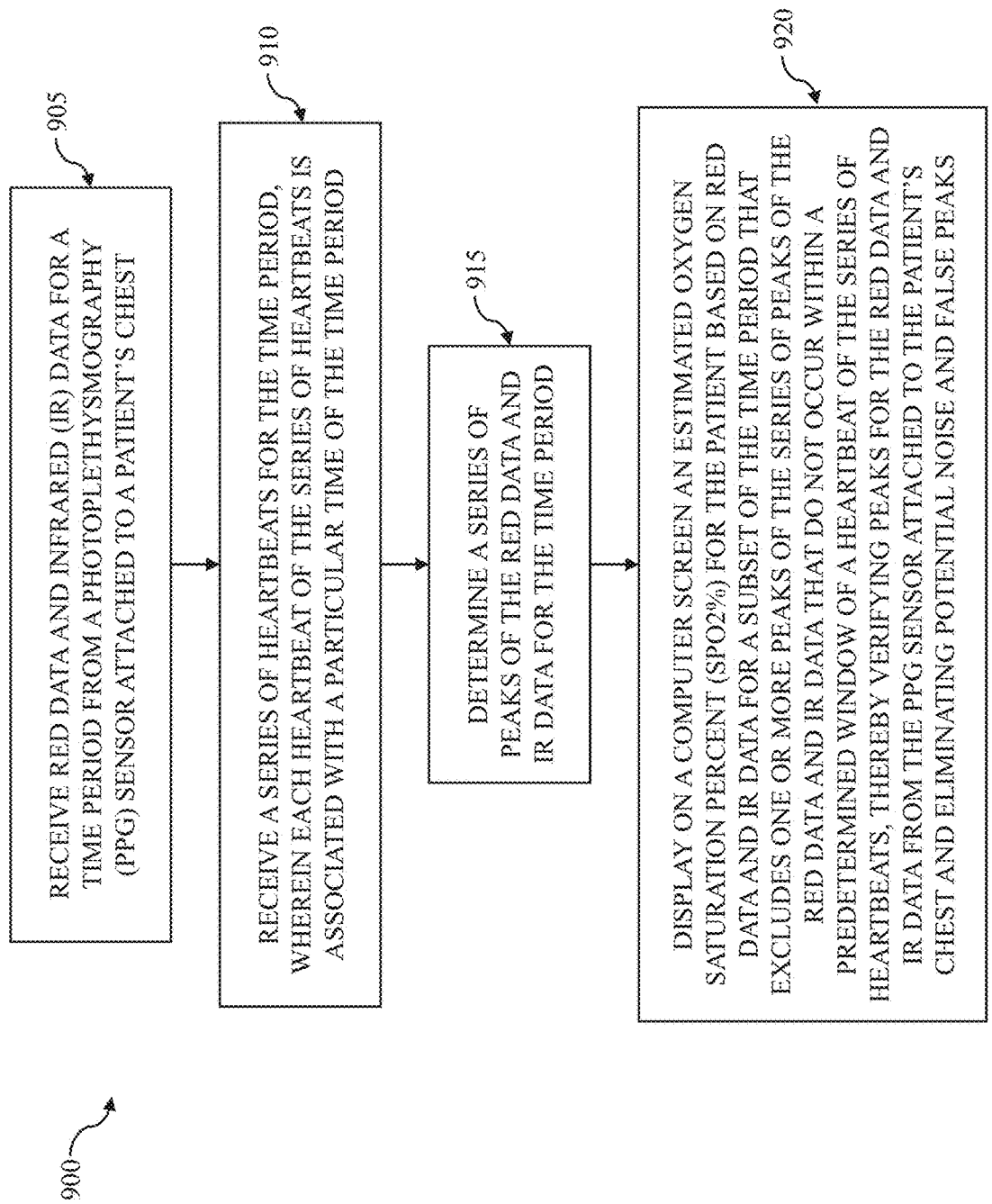
FIG. 9 illustrates a first flow chart of a first process according to various embodiments of the present disclosure.

As set forth in FIG. 9, systems discussed herein may derive an estimated SpO2% for a patient by proceeding in a manner as illustrated by process 900. The process 900 may begin at block 905 by first receiving red data and IR data for a time period from a PPG sensor attached to the patient's chest. The process may proceed to block 910 by receiving a series of heartbeats for the time period, wherein each heartbeat of the series of heartbeats is associated with a particular time of the time period. The process may proceed to block 915 by determining a series of peaks of the red data and IR data for the time period. After determining the series of peaks, the process may proceed to block 920 by displaying on a computer screen an estimated SpO2% for the patient based on red data and IR data for a subset of the time period that excludes one or more peaks of the series of peaks of the red data and IR data that do not occur within a predetermined window of a heartbeat of the series of heartbeats, thereby verifying peaks for the red data and IR data from the PPG sensor attached to the patient's chest and eliminating potential noise and false peaks.

The predetermined window may any suitable window of time. In at least one embodiment, the predetermine window is a window of 0.2-1.0 seconds. In various embodiments, the predetermined window is 0.1-1.2 seconds. In at least one embodiment, the predetermined window is based on an average human heartbeat and/or an average heartbeat of the patient, either predetermined or measured by the system.

As illustrated in FIG. 10, systems discussed herein may derive an estimated SpO2% for a patient by proceeding in a manner as illustrated by process 1000. The process 1000 may begin at block 1005 by first receiving, from a processor attached to a patient's chest, red data, IR data, and a series of heartbeats for a time period. The processor may be communicably coupled to: a PPG sensor for providing the red data and IR data; an ECG sensor, an accelerometer, and/or a beat detector for providing the series of heartbeats; and the processor may use a single clock to associate the red data, the IR data, and the series of heartbeats with the time period. The process may proceed to block 1010 by determining a series of peaks of the red data and IR data for the time period. The process may then proceed to block 1015 by computing a subset of the red data and IR data by excluding any peaks of the series of peaks that do not correspond with a heartbeat of the series of heartbeats, thereby verifying peaks for the red data and IR data from the PPG sensor attached to the patient's chest and eliminating potential noise and false peaks. The process may proceed to block 1020 by estimating an SpO2% for the patient by computing a ratio of the red data and IR data included in the subset. After the SpO2% is estimated, the process may then proceed to block 1025 by displaying on a computer screen the estimated SpO2% for the patient.

The present disclosure provides systems and processes in order to improve and optimize the PPG signal quality of those patients with highly pigmented skin. Predetermined intervals may allow for adjustments to settle and to maintain the red and IR intensities in a given range. The red and IR drive currents may be adjusted independently or by adjusting an analog-to-digital full scale range (ADC FSR). The process may have two main states: adjustment of LEDs; and adjustment of the ADC FSR. When the red and IR intensities are not in a set range, the system may adjust the LEDs by increasing or decreasing the drive intensity in small increments. If the measured red and IR intensities are still not in range after reaching a maximum or minimum drive intensity, then the system may adjust the ADC FSR to provide a larger or smaller overall gain. After this adjustment, the system may repeat the process of adjusting the LEDs until the red and IR intensities are in range.

Figure 11:
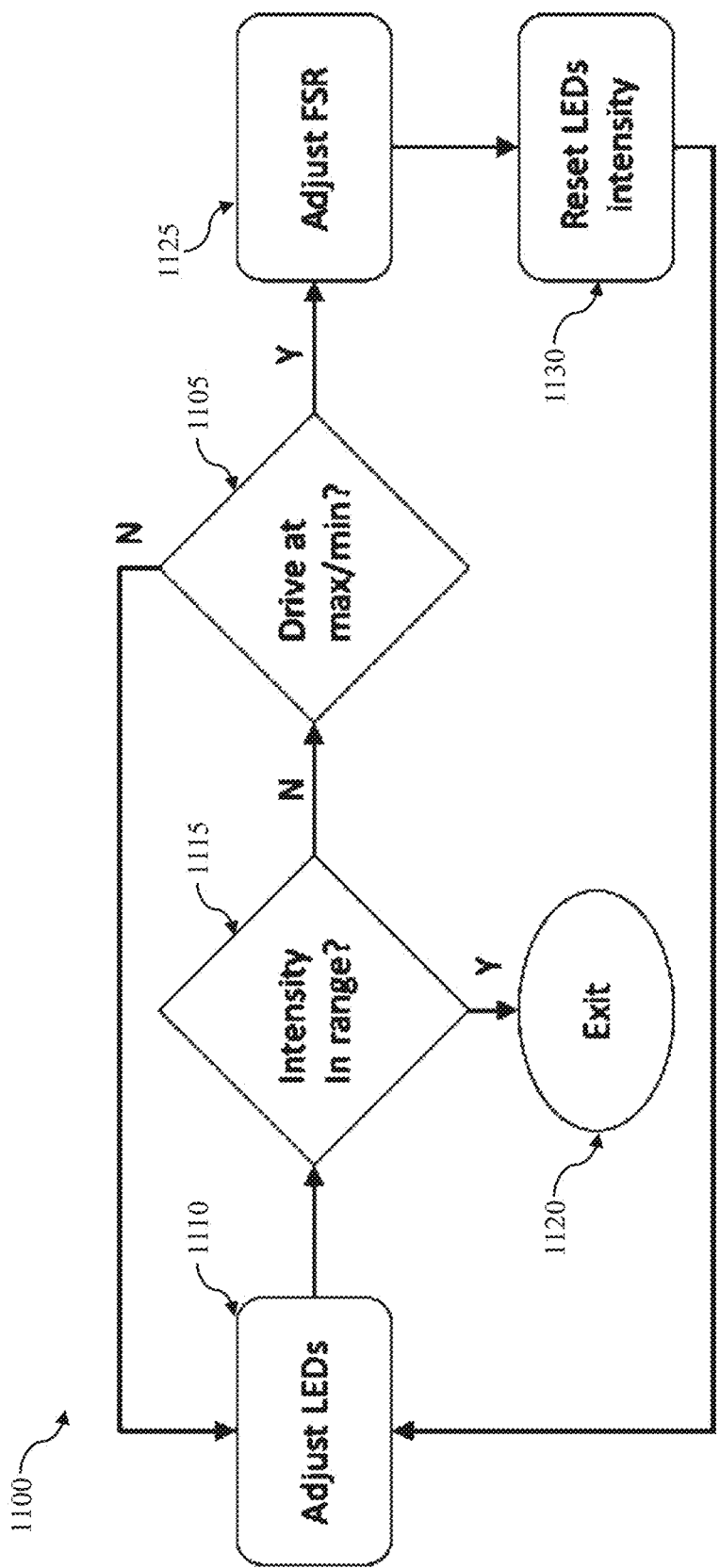
FIG. 11 illustrates a third flow chart of a third process according to various embodiments of the present disclosure.

As set forth in FIG. 11, the systems discussed herein may run a process 1100 to determine whether the red and IR light intensities are at a sufficient level. The system may begin the process 1100 when the system detects a poor PPG signal quality. According to one embodiment, poor PPG signal quality may be identified using a low amplitude AC component of the PPG signal or using an insufficient DC signal. In order to determine an AC signal amplitude, an AC component may be extracted from the PPG signal, and a peak estimator may be employed in order to detect the AC peaks. The process 1100 may begin at block 1105 determining whether the drive intensity is at a maximum or minimum. If not, then the system may proceed to block 1110 by adjusting the LEDs. After adjusting, the system may proceed to block 1115 by determining whether the intensity is in range. Such "range" may be a range experimentally determined for the sensor (e.g., a minimum ADC above a noise threshold). If yes, then the system may proceed to block 1120 by exiting the process 1100. If the intensity is not in range, then the system may proceed to block 1105 by determining whether the drive intensity is at a maximum or minimum. If yes, then the system may proceed to block 1125 by adjusting the ADC FSR. After adjusting the ADC FSR, the system may proceed to block 1130 by resetting the LED light intensity and proceed to adjusting the LEDs.

Figure 12:
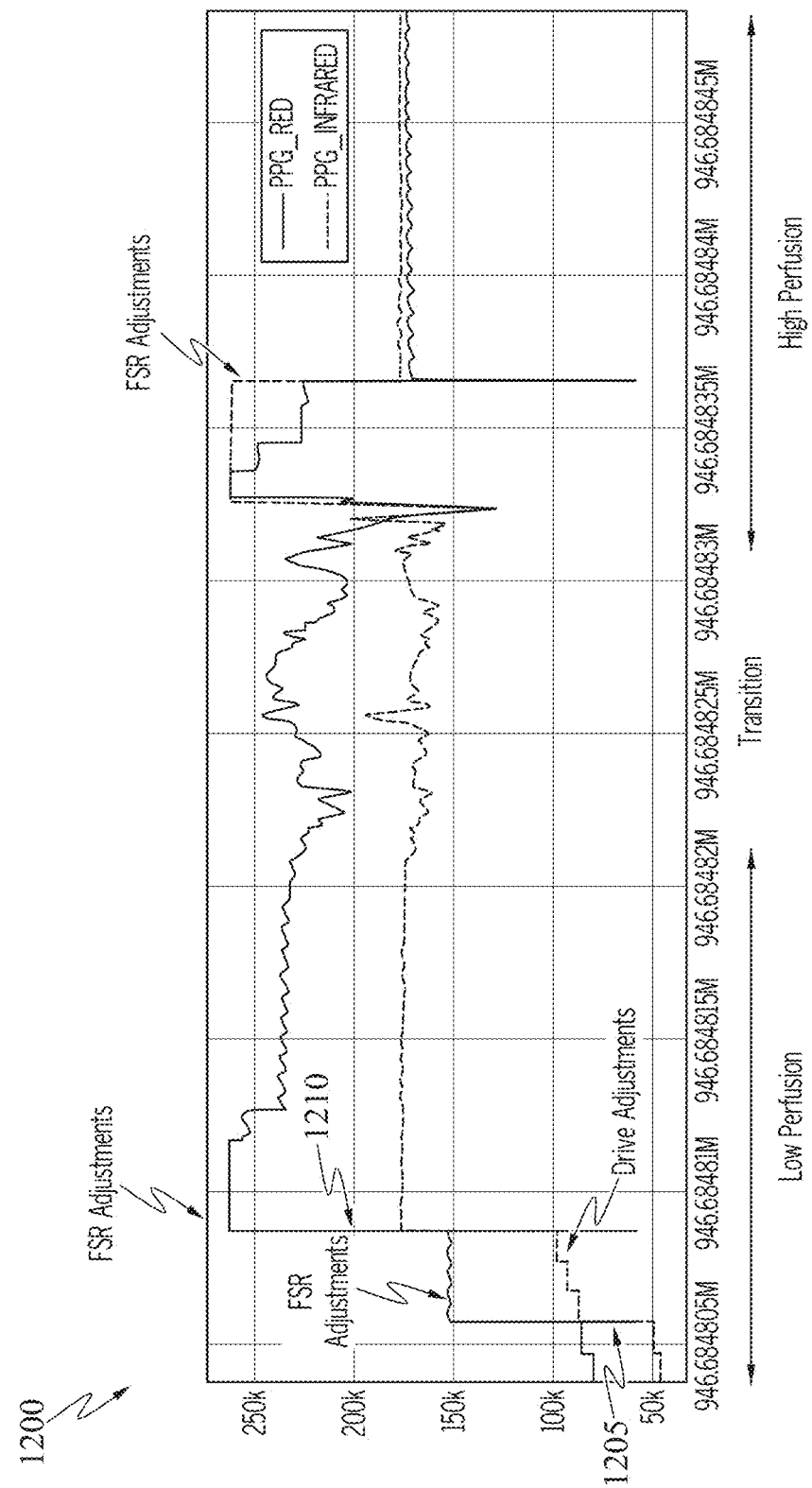
FIG. 12 illustrates a first graph according to various embodiments of the present disclosure.

As illustrated in FIG. 12, certain data points may be collected via tests performed on the effectiveness of the process as described herein, as illustrated by graph 1200, which may be associated to the "range" as described with reference to FIG. 11. One test may include two steps: (1) placing an optical filter between a patient's finger and the PPG sensor; and (2) removing the optical filter to assess the ability of the process to revert back to the original settings of the intensities and the FSR value. The red/IR optical filter may reduce red signal intensity without attenuating the IR signal, simulating a highly pigmented tissue bed. After placing the optical filter between the finger and the PPG sensor, the device may be given a few seconds to adjust to the tissue properties. The results of this test are shown in FIG. 12. With the optical filter present, the initial value of red and IR may or may not be sufficiently increased with drive currently only. Therefore, the FSR is adjusted (as illustrated by the first large jump 1205 in FIG. 12). The IR signal may be in range, but the red may be too low. Therefore, the red drive is increased in two steps, and since it may be still below the threshold, the FSR is increased again (as illustrated by the second large jump 1210 in FIG. 12). The red signal may be in range, but the IR signal may be saturated. The drive intensity for IR may be reduced, such that the two signals may be both in range. Similar behavior can be observed once the filter is removed.

Figure 13:
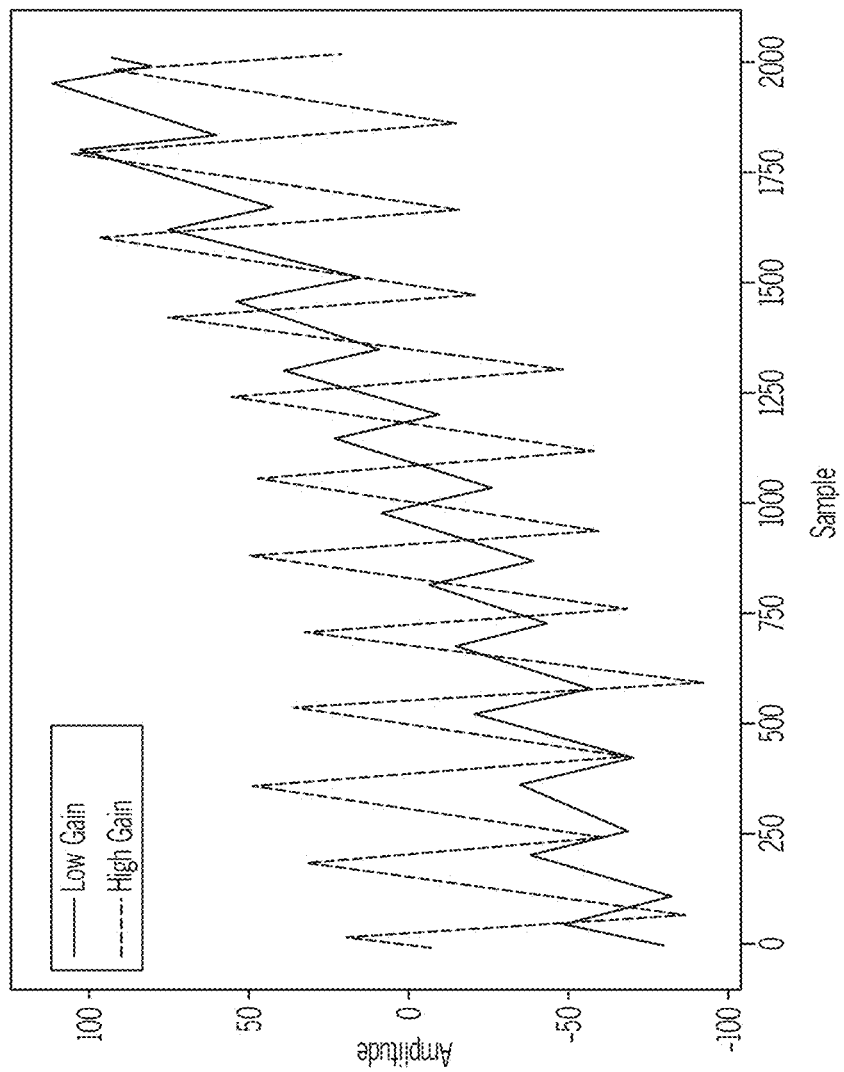
FIG. 13 illustrates a second graph according to various embodiments of the present disclosure.
Figure 14:
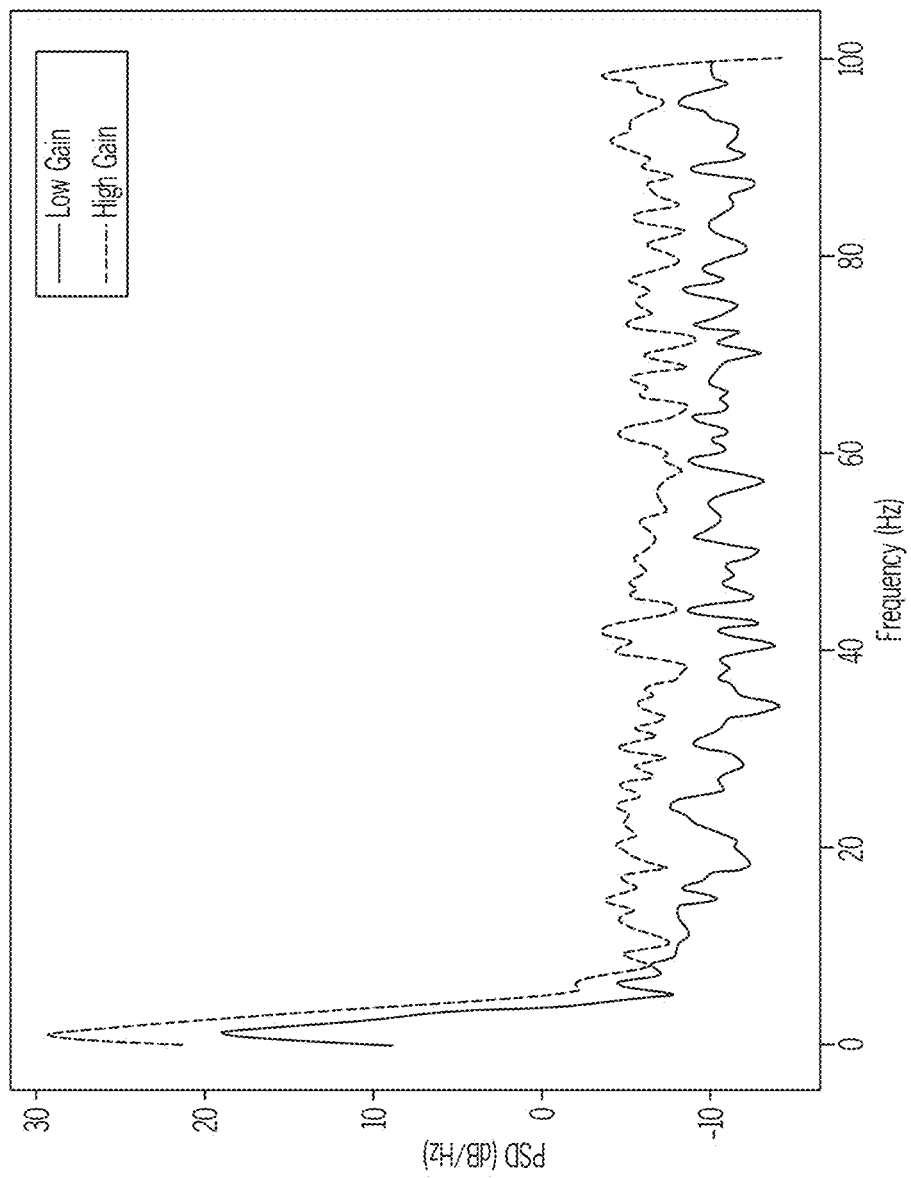
FIG. 14 illustrates a third graph according to various embodiments of the present disclosure.

FIG. 13 illustrates a time domain comparison of pulses, as illustrated by graph 1300. As illustrated, the magnitude of the pulses may increase in the "high gain" case, which may lead to easier pulse detection in SpO2 and pulse rate processes. FIG. 14 illustrates similar segments in a frequency domain, as illustrated by graph 1400. As illustrated, the noise floor of the high gain segment may be 4 decibels higher, but the signal peak may be 10 decibels stronger. Such increased signal peak may result in 6 decibels of SNR improvement.

Figure 15:
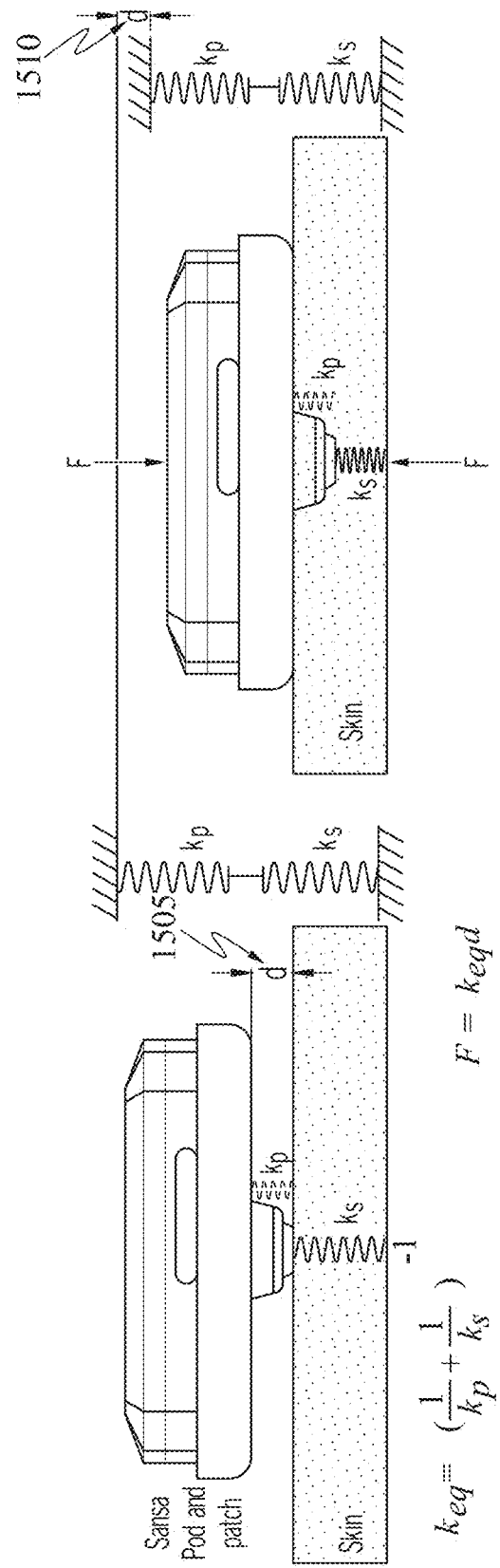
FIG. 15 illustrates a force exerted by a PPG sensor according to various embodiments of the present disclosure.
Figure 16:
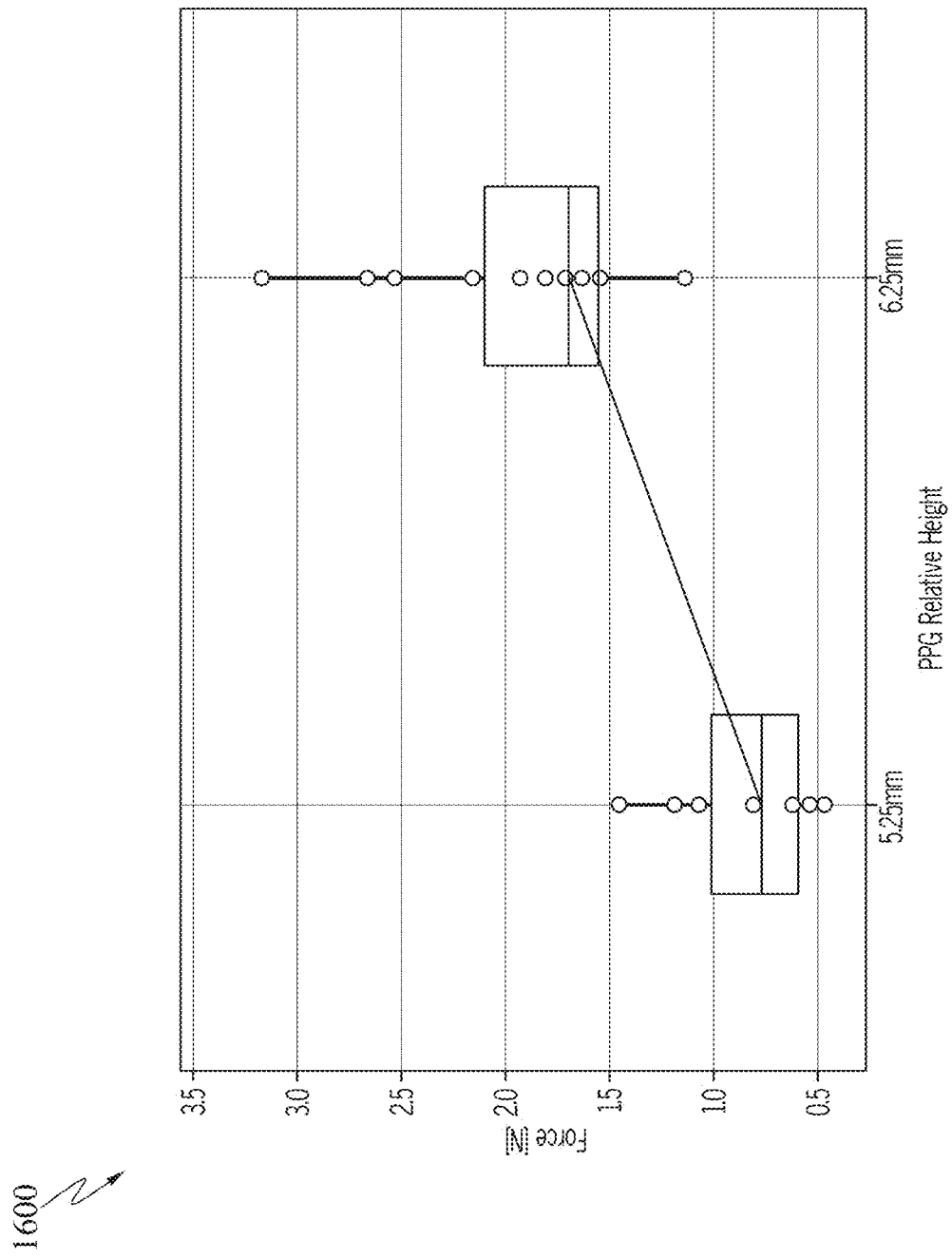
FIG. 16 illustrates a fourth graph according to various embodiments of the present disclosure.

As illustrated in FIG. 15, an increase in the height of PPG sensor (d), as illustrated by 1505 and 1510, respectively, may lead to an increase in force applied to the skin through the PPG sensor ($F=k_{eq}d$). FIG. 16 illustrates a set of data points associated with the results of two fixed PPG height values (the first at 5.25 mm, the second at 6.25 mm), as illustrated by graph 1600. As illustrated, there is a direct correlation between the height and the force (with a p-value of 0.000). Force may have many effects on the PPG signal, including, but not limited to: reduction of the motion artifacts; reduction of the effects of venous pulse and respiratory noise on PPG pulse; providing of proper contact and coupling between the PPG sensor and the patient's skin; increasing the depth of light penetration, which may lead to higher pulse amplitude and SNR; decrease of the effects of movement on sensor and skin contact status; and reduction of the stiffness of blood vessels by balancing internal and external pressure, which may lead to higher pulse amplitude.

Figure 17:
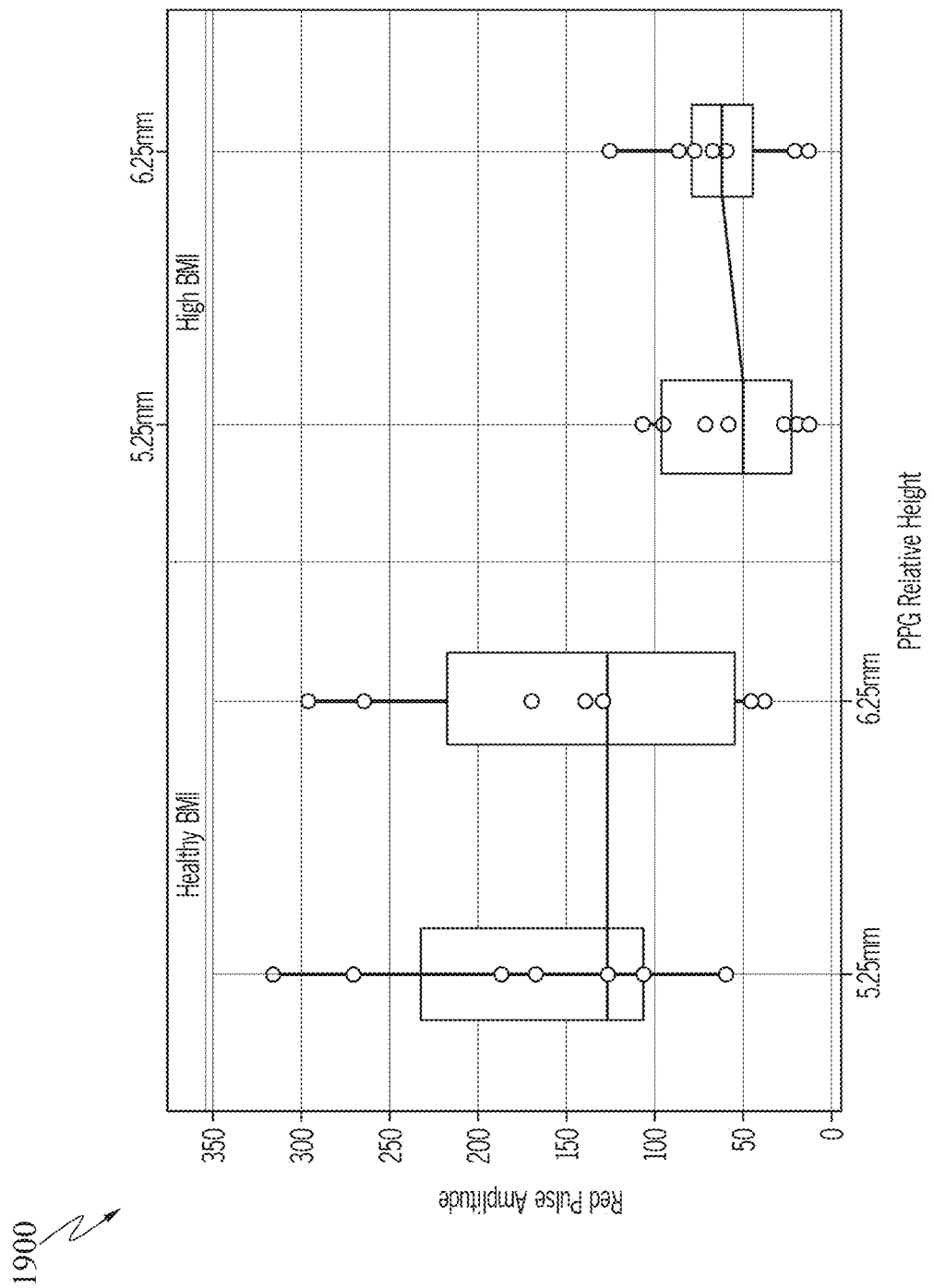
FIG. 17 illustrates a fifth graph according to various embodiments of the present disclosure.
Figure 18:
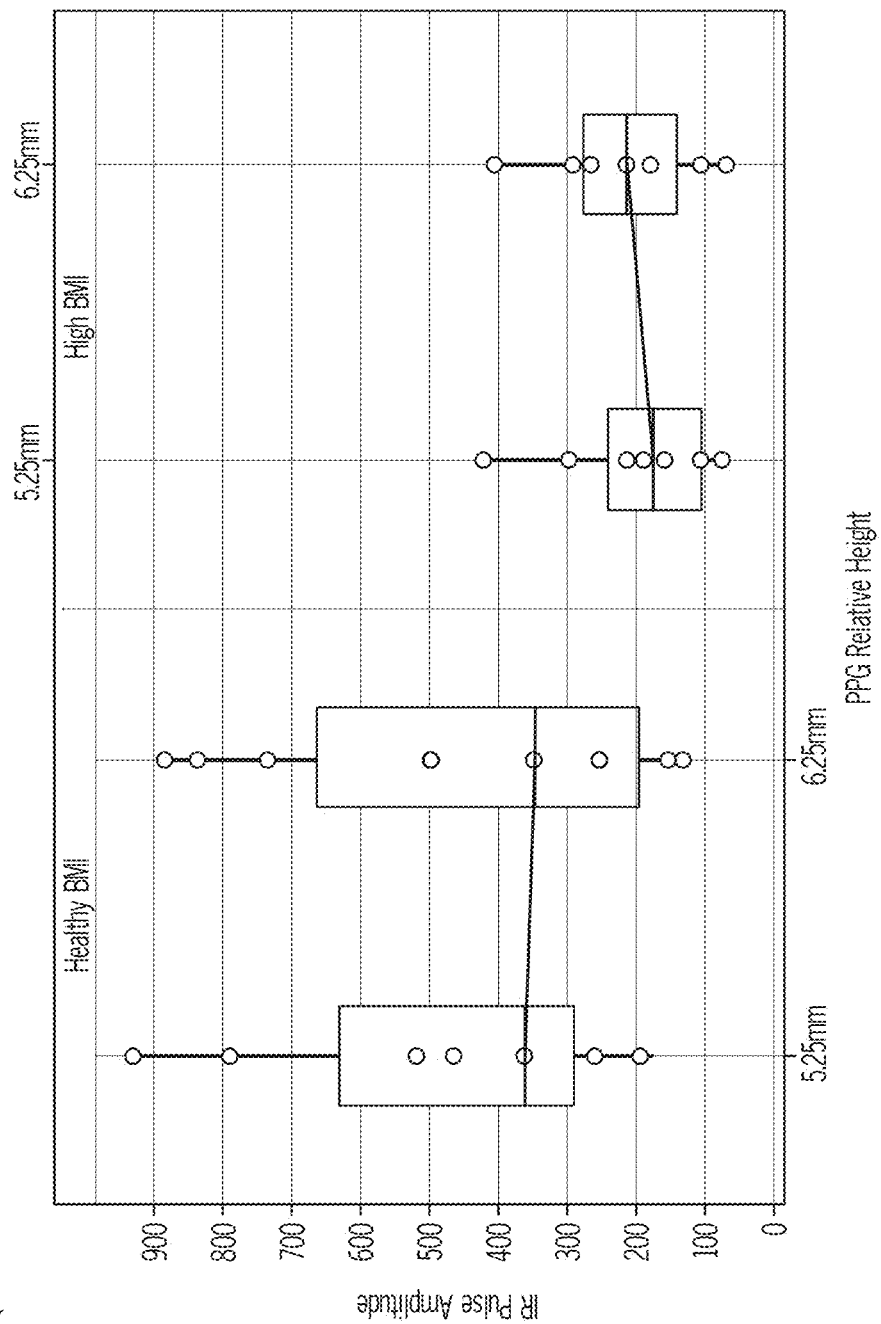
FIG. 18 illustrates a sixth graph according to various embodiments of the present disclosure.
Figure 19:
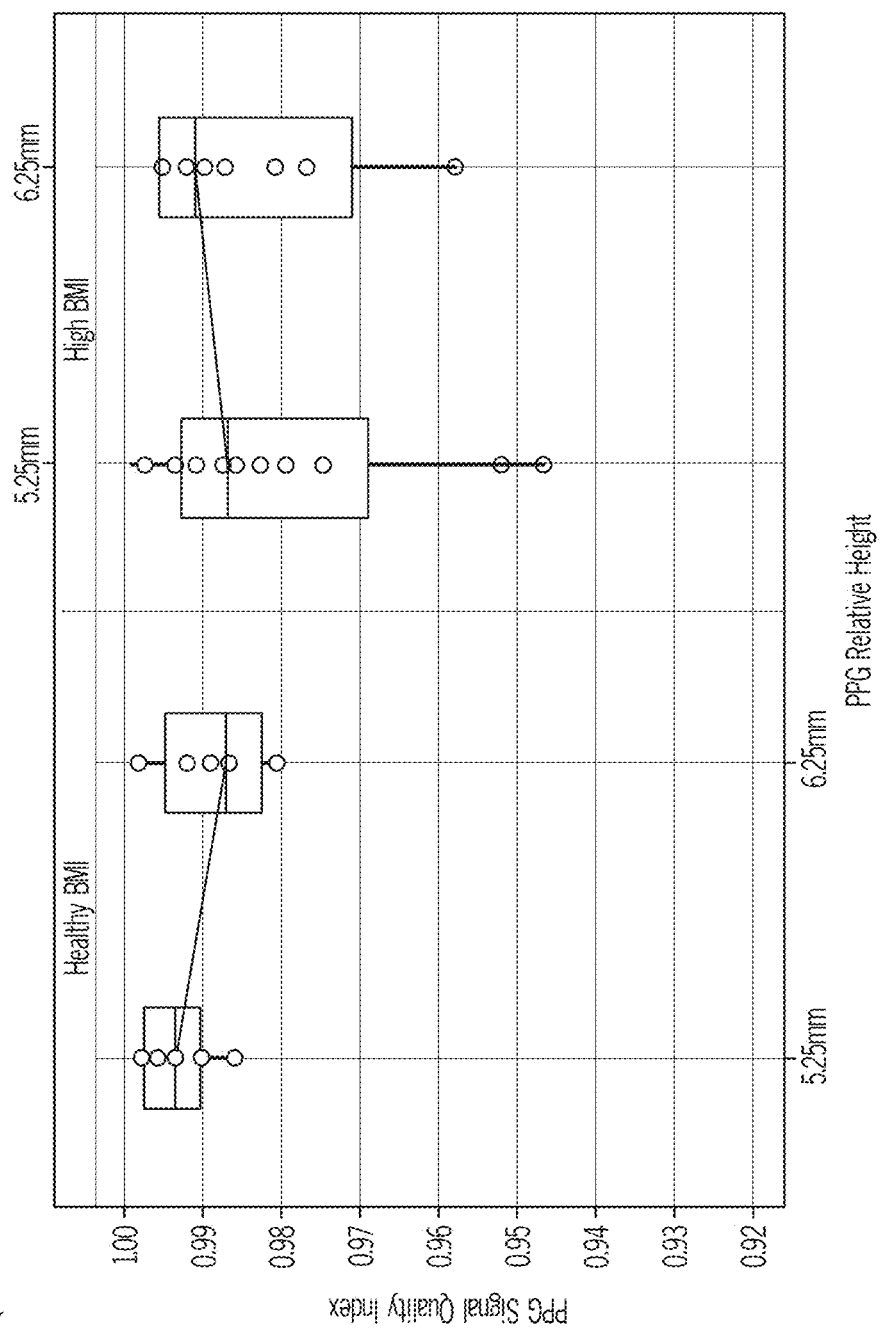
FIG. 19 illustrates a seventh graph according to various embodiments of the present disclosure.
Figure 20:
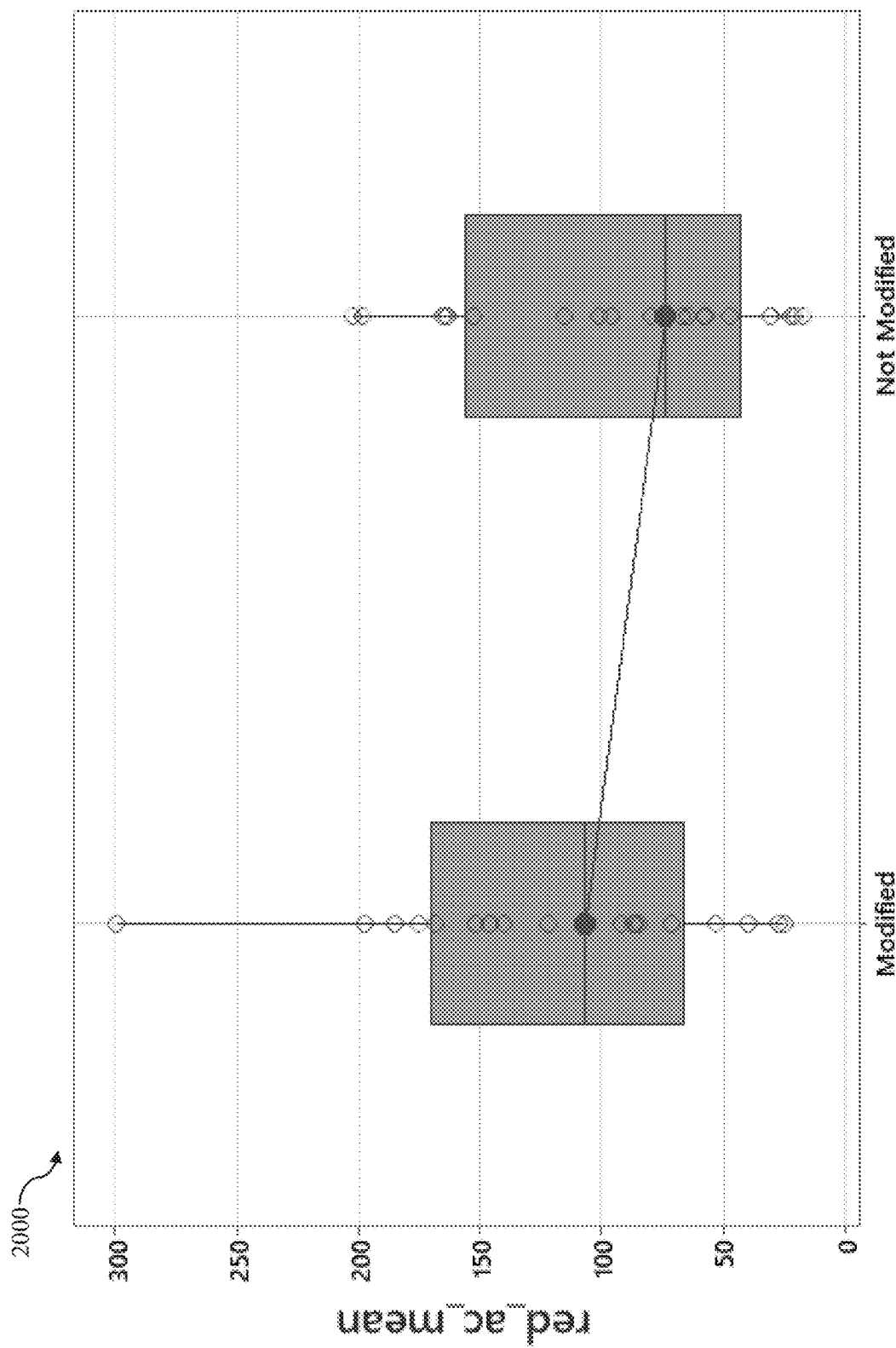
FIG. 20 illustrates an eighth graph according to various embodiments of the present disclosure.
Figure 21:
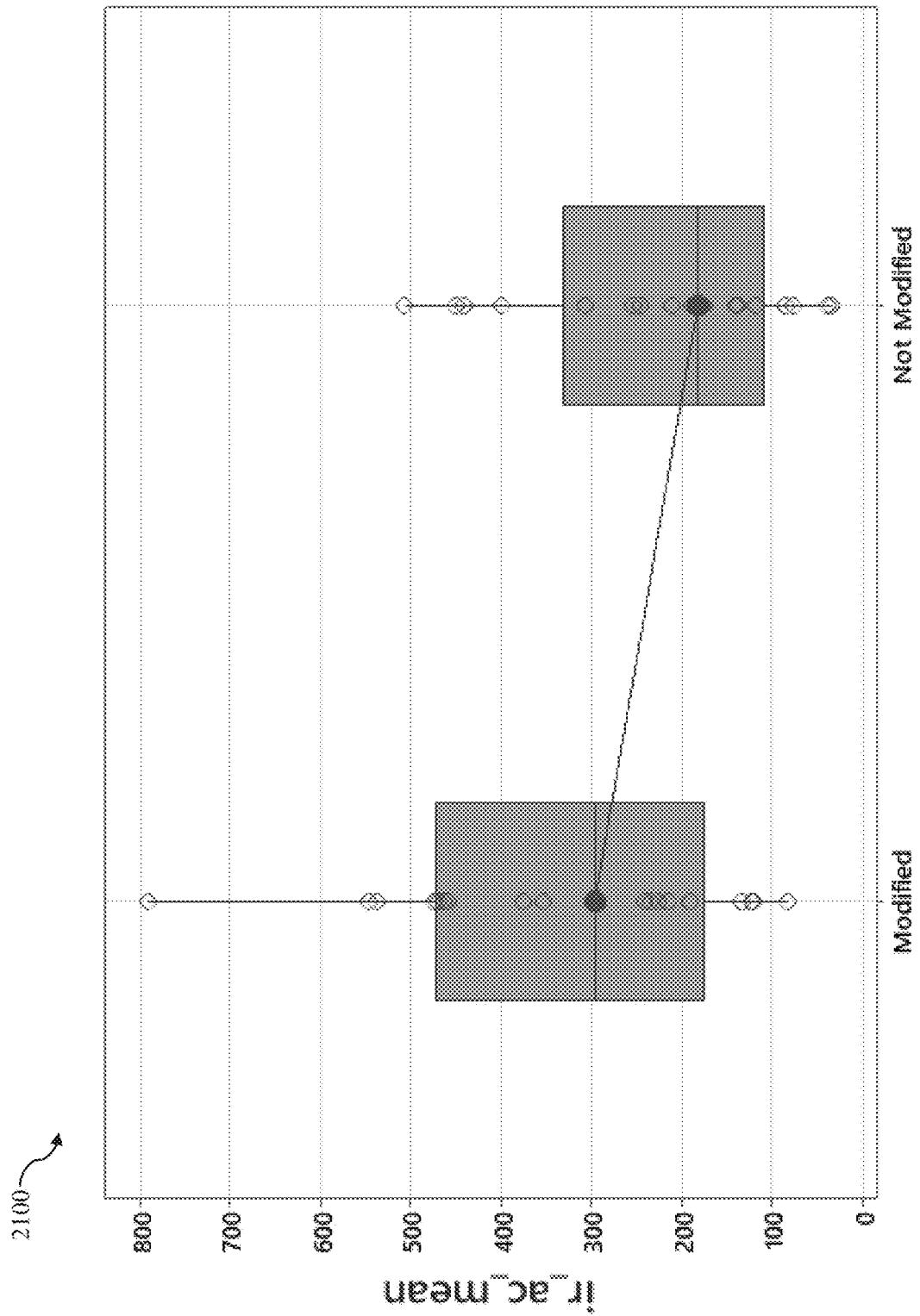
FIG. 21 illustrates a ninth graph according to various embodiments of the present disclosure.

As set forth in FIGS. 17-19, the PPG height and the force may be optimized for BMI and signal quality. The increase in the height of the PPG sensor may lead to: an overall decrease in PPG pulse amplitude and signal quality in subjects with a BMI less than 30; and an overall increase in PPG pulse amplitude and signal quality in subjects with a BMI greater than or equal to 30. As illustrated by the data points in FIGS. 17-19, as illustrated by graphs 1700, 1800, and 1900, respectively, the PPG height of 5.25 mm may provide optimum PPG performance for users with various different BMIs (e.g., 20 to 63 kg/m$^2$).

In various embodiments, a device herein may include a mechanism to adjust a height of a PPG sensor (with respect to a bottom of patch) to dynamically adjust the PPG height while the PPG sensor is worn by a patient. In these embodiments, the device includes actuator, hydraulic cylinder, etc. that may be controlled by a processor. In further embodiments, upon the system determining that PPG signal quality is low or a SQI metric varies or is low, the system/processor may adjust a height of the PPG sensor to increase force for the benefits discussed herein. The system may also adjust the LEDs and/or ADC FSR to compensate for low PPG signal quality in addition to or instead of adjusting a height of the PPG sensor.

According to particular embodiments, a physician may measure a BMI of a patient prior to prescribing a particular patch/device. In these embodiments (and others), a physician measures a BMI of a patient and selects a patch with a particular PPG height (based on a chart or software calculation). In at least one embodiment, patches/devices discussed herein are sold with varying PPG heights, corresponding to different BMI measurements. Stated differently, based on a patient's BMI, a physician or other provider (or the patient) may select a patch/device with a PPG height to provide optimal PPG signal quality.

As will be understood, opposed to (or in addition to) adjusting PPG height to increase force, compliance of the patch in between the PPG sensor and the skin can be adjusted to adjust force (cutout represents infinite compliance). Upon determining a patient's BMI, adhesive or select materials of a device/patch may be adjusted to adjust compliance of the patch between the PPG sensor and patient's skin.

Figure 22:
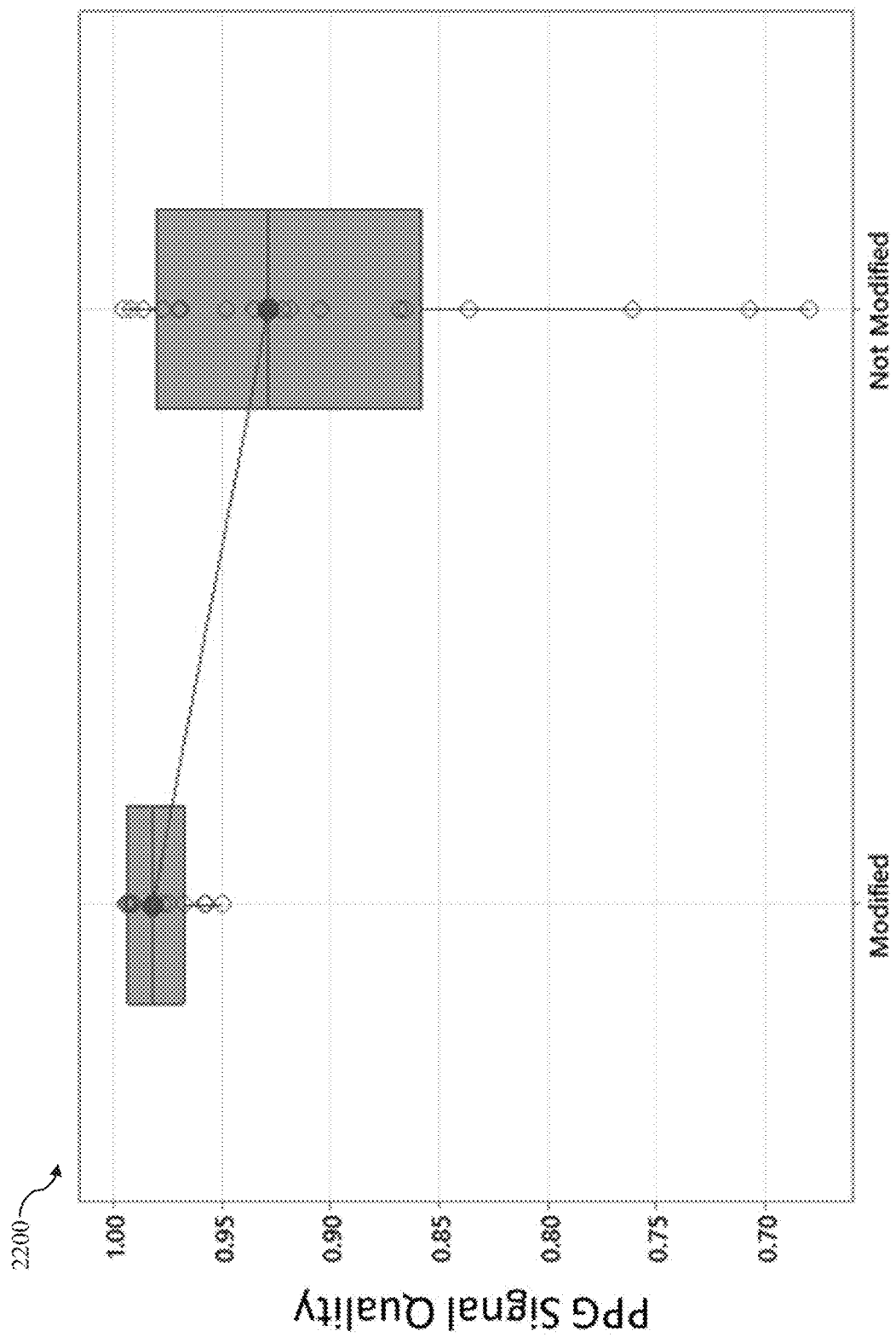
FIG. 22 illustrates a tenth graph according to various embodiments of the present disclosure.
Figure 23:
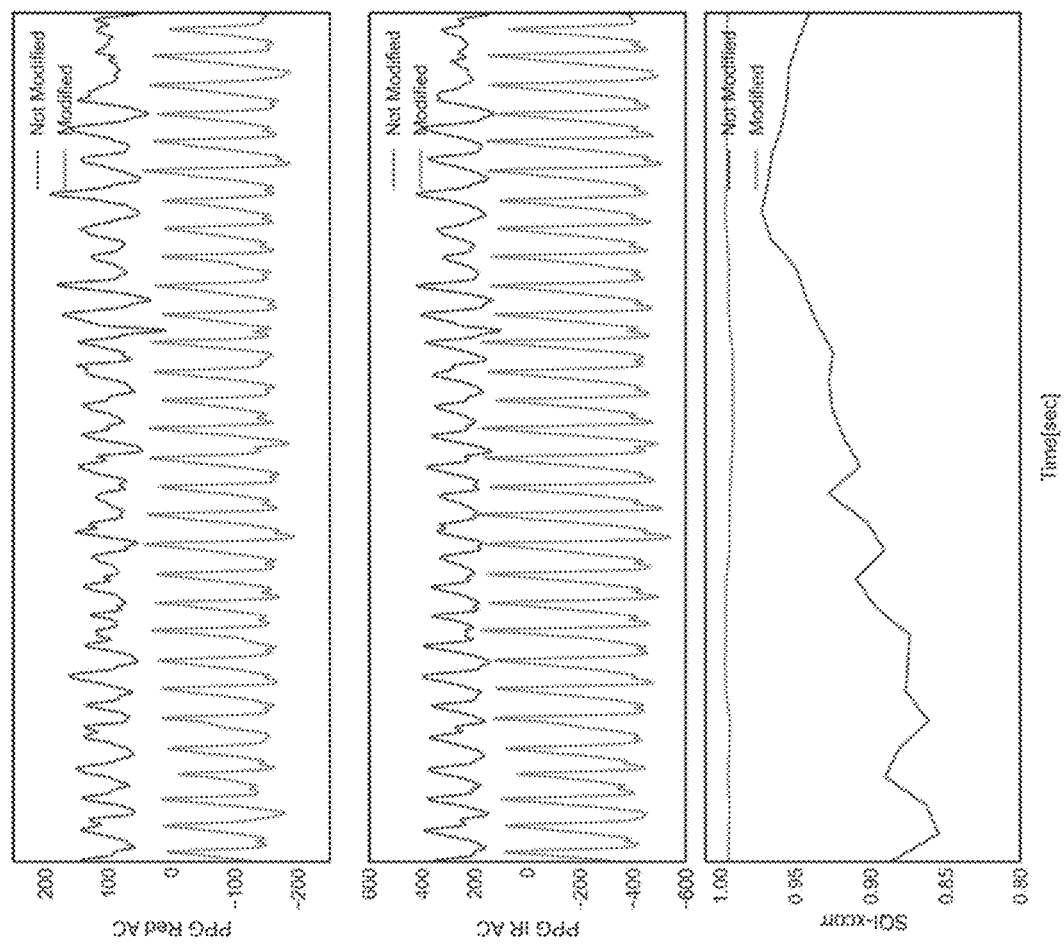
FIG. 23 illustrates an eleventh graph according to various embodiments of the present disclosure.

As set forth in FIGS. 20-23, the configuration of the patch on the patient may have an impact on the amplitude of red signal (see graph 2000 in FIG. 20), the amplitude of IR signal (see graph 2100 in FIG. 21), and PPG signal quality (see graph 2200 in FIG. 22). As illustrated, there may be an impact when the patch is in a "modified" configuration versus in a "not modified" configuration. When "modified," there may be a cutout in the patch which may allow for more force to applied against the patient's skin. When "unmodified," there may not be a cutout in the patch, and as such, there may be restricted protrusion of the PPG sensor against the patient's skin. The cutout may allow for a user to adjust the force of the patch in between the PPG sensor and the skin. The height of the protrusion may vary, and the patch between the PPG sensor and the skin may be modified in order to achieve certain impacts as disclosed in FIGS. 20-22. Graph 2300 of FIG. 23 illustrates a set of data points associated with the "modified" and "not modified" patch configuration. As illustrated, the "modified" configuration may lead to a higher signal quality with respect to amplitude of red signal, amplitude of IR signal, and/or PPG signal quality.

The present disclosure is directed to increasing the PPG contact force through an increase in the height of the PPG sensor (which may result in an increase in an air gap between a bottom of a PPG sensor and a bottom of the patch) in order to improve and optimize the PPG signal quality of those patients with high BMIs. An increase in the height of the PPG sensor (or the depth of penetration) may lead to an increase in the force applied to the skin through the PPG sensor.

Force affects the PPG signal quality in many ways, including: reducing the motion artifacts; reducing the effects of venous pulse and respiratory noise on PPG pulse; providing proper contact and coupling between the PPG sensor and the patient's skin; increasing the depth of light penetration which may lead to higher pulse amplitude and SNR; decreasing the effects of movement on the status of the contact between the PPG sensor and the patient's skin; and reducing the stiffness of blood vessels by balancing internal and external pressure which may lead to higher pulse amplitude. Overall, increasing the height of the PPG sensor with patients with a high BMI also increases the PPG pulse amplitude and signal quality. A PPG sensor height of 5.25 mm may provide the optimum PPG performance for users at any point in a large range of BMIs (e.g., 20 to 63).

Figure 24:
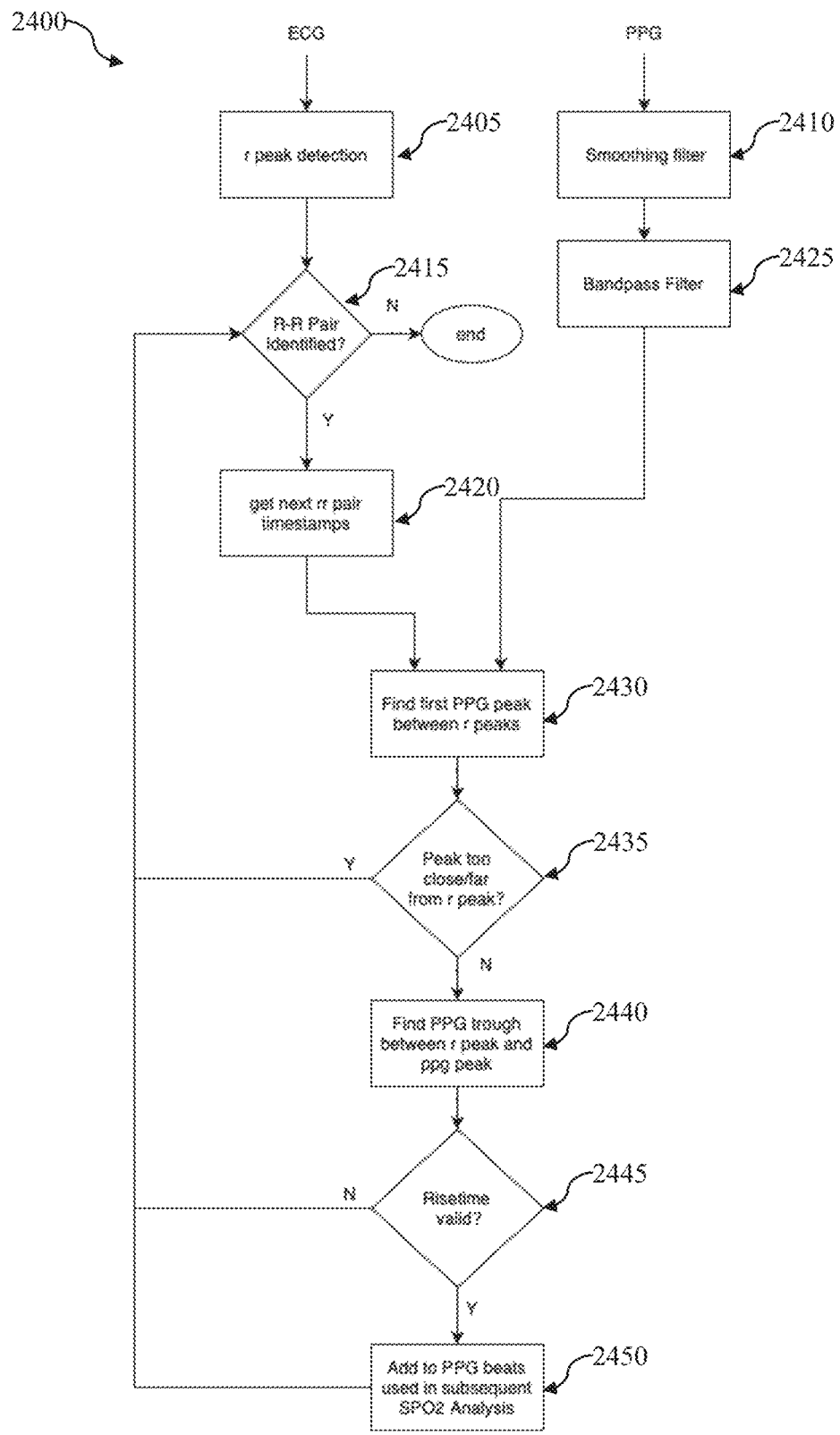
FIG. 24 illustrates a fourth flow chart of a fourth process according to various embodiments of the present disclosure.

As will be understood from discussions herein, the system may determine whether a detected PPG peak or beat is related to pulsatile blood flow, opposed to noise (e.g., movement, etc.). In various embodiments, the system uses a combination of ECG data and PPG data to make such a determination. As illustrated in FIG. 24, a process 2400 may begin at block 2405 and 2410 for ECG signal and PCG signal, respectively. For ECG signal, the process 2400 may begin at block 2405 by detecting R-wave peaks in the ECG signal (e.g., heartbeats). After detecting such R-wave peaks, the process 2400 may proceed to block 2415 to identify an R-R pair. If the system cannot identify such pair, then the process 2400 may end. However, if the system can identify an R-R pair, then the process 2400 may proceed to block 2420 to retrieve the R-R pair timestamps. Simultaneously or separately, the system may run process 2400 with respect to the PCG signal. The process 2400 for the PPG signal may begin at block 2410 by applying a smoothing filter to the PPG signal. The process 2400 may proceed to block 2425 by applying a bandpass filter to the PPG signal.

Upon completing at least one of block 2420 or 2425, the process 2400 may proceed to block 2430 by finding a first PPG peak between the R peaks (e.g., R peaks and PPG peak are synchronized via a clock, clocks, or PPT, as discussed herein). The process 2400 may then proceed to block 2435 by determining whether the PPG peak is too close or too far from the R peak (too close or too far may be based on time or signal distance, such as outside the time of a normal pair of heart beats). If yes, then the process 2400 may proceed back to block 2415. If no, then the process 2400 may proceed to block 2440 by finding a PPG trough between the R peak and the PPG peak. The process may then proceed to block 2445 by determining whether the risetime is valid (e.g., whether the rise time between the PPG trough and the PPG peak is within an acceptable range). If no, then the process 2400 may proceed back to block 2415. If yes, then the process 2400 may proceed to block 2450 by adding to the PPG beats used in a subsequent SpO2 analysis. The process 2400 may then loop back in a repetitive fashion back to block 2415.

Aspects, features, and benefits of the systems and processes discussed herein will become apparent from the information disclosed in the exhibits. The embodiments were chosen and described in order to explain the principles of the systems and processes and their practical application so as to enable others skilled in the art to utilize the systems and processes and various embodiments and with various modifications as are suited to the particular use contemplated. Alternative embodiments will become apparent to those skilled in the art to which the present systems and processes pertain without departing from their spirit and scope.

Accordingly, the scope of the present systems and processes is defined by the appended claims rather than the foregoing description and the exemplary embodiments described therein.

From the foregoing, it will be understood that various aspects of the processes described herein are software processes that execute on computer systems that form parts of the system.

Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed systems and processes may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems and processes are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems and processes will be readily discernible from the description herein, by those of ordinary skill in the art. Many embodiments and adaptations of the disclosure and claimed systems and processes other than those herein described, as well as many variations, modifications, and equivalent arrangements and methodologies, will be apparent from or reasonably suggested by the disclosure and the foregoing description thereof, without departing from the substance or scope of the claims.

Furthermore, any sequence(s) and/or temporal order of steps of various processes described and claimed herein are those considered to be the best mode contemplated for carrying out the claimed systems and processes. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems and processes. In addition, some steps may be carried out simultaneously, contemporaneously, or in synchronization with other steps.

The embodiments were chosen and described in order to explain the principles of the claimed systems and processes and their practical application so as to enable others skilled in the art to utilize the systems and processes and various embodiments and with various modifications as are suited to the particular use contemplated. Alternative embodiments will become apparent to those skilled in the art to which the claimed systems and processes pertain without departing from their spirit and scope. Accordingly, the scope of the claimed systems and processes is defined by the appended claims rather than the foregoing description and the exemplary embodiments described therein.

Any logic or application described herein may be implemented and structured in a variety of ways. For example, one or more applications described may be implemented as modules or components of a single application. Further, one or more applications described herein may be executed in shared or separate computing systems or a combination thereof. For example, more than one application may execute in the same computing system, or in multiple computing systems in the same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A system for deriving an estimated oxygen saturation percentage (SpO2%) for a patient comprising:
   a patch configured for attaching to skin of a patient and comprising:
      a photoplethysmography (PPG) sensor for providing reflectance red data and infrared (IR) data;
      a bottom surface located at a height from the PPG sensor of greater than 1 mm, wherein upon attaching the bottom surface to the patient, the PPG sensor is pressed into the skin of the patient thereby increasing amplitude of the red data and IR data;
      a heartbeat detector comprising electrocardiogram (ECG) sensor, an accelerometer, a bioimpedance sensor, and/or a beat detector for providing a series of heartbeats; and
      a radio for transmitting the red data, the IR data, and the series of heartbeats, wherein the red data, the IR data, and the series of heartbeats are associated with a time period; and
   a processor configured to:
      receive, from the radio, the red data, the IR data, and the series of heartbeats associated with the time period, the red data having a mean AC amplitude value of about 100 and the IR data having a mean AC amplitude value of about 300;
      compute a series of peaks of the red data and IR data for the time period;
      compute a subset of the red data and IR data by excluding any peaks of the series of peaks that do not correspond with a heartbeat of the series of heartbeats, thereby verifying peaks for the red data and IR data and eliminating potential noise and false peaks;
      estimate an oxygen saturation percentage (SpO2%) for the patient by computing an optical ratio of the red data and IR data included in the subset; and
      display on a computer screen the estimated SpO2% for the patient.

2. The system of claim 1, wherein:
   the subset of the red data and IR data comprises a particular peak of the series of peaks at a particular time;
   the series of heartbeats includes a particular heartbeat occurring within a predetermined window of the particular time; and
   the estimated SpO2% for the patient is based on the particular peak.

3. The system of claim 2, wherein the processor is configured to estimate the SpO2% by:
   splitting the subset of the red data and IR data into alternating current (AC) and direct current (DC) components; and
   estimating the patient's SpO2% by the optical ratio expressed as:

$$R = \frac{AC_{rms\,RED} / DC_{rms\,RED}}{AC_{rms\,IR} / AC_{rms\,IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

4. The system of claim 3, wherein the time period is derived from a single clock or two or more synchronized clocks.

5. The system of claim 1, wherein:
   each peak of the series of peaks corresponds with a specific time of the time period; and
   a specific peak of the series of peaks does not correspond with a heartbeat of the series of heartbeats if there is no heartbeat within a predetermined window of the specific time corresponding with the specific peak.

6. The system of claim 1, wherein the system is configured to determine a predicted diagnosis of sleep apnea based on at least one of the red data, the IR data, and the series of heartbeats.

7. A system for deriving an estimated oxygen saturation percentage (SpO2%) for a patient comprising:
   at least one processor communicably coupled to a patch for affixing to a patient and configured to:
      receive reflectance red data and IR data derived from a photoplethysmography (PPG) sensor coupled to the patch and associated with a time period, wherein:

the patch comprises a bottom surface located at a height from the PPG sensor of greater than 1 mm, upon attaching the bottom surface to the patient, the PPG sensor is pressed into the skin of the patient thereby increasing amplitude of the red data and IR data, and the red data has a mean AC amplitude value of about 100 and the IR data has a mean AC amplitude value of about 300;

receive a series of heartbeats associated with the time period and derived from a heartbeat detector, the heartbeat detector comprising an electrocardiogram (ECG) sensor, an accelerometer, bioimpedance sensor, and/or a beat detector coupled to the patch;

compute a series of peaks of the red data and IR data for the time period;

compute a subset of the red data and IR data by excluding any peaks of the series of peaks that do not fall within a predetermined time window of a heartbeat of the series of heartbeats;

estimate an oxygen saturation percentage (SpO2%) for the patient by computing an optical ratio of the red data and IR data included in the subset, thereby verifying peaks for the red data and IR data and eliminating potential noise and false peaks; and display on a computer screen the estimated SpO2% for the patient.

8. The system of claim 7, wherein the red data, the IR data, and the series of heartbeats are associated with the time period via one or more clocks of a processor coupled to the patch.

9. The system of claim 8, wherein:
the subset of the red data and the IR data comprises a particular peak of the series of peaks at a particular time;
the series of heartbeats includes a particular heartbeat occurring within the predetermined time window of the particular time; and
the estimated SpO2% for the patient is based on the particular peak.

10. The system of claim 9, wherein the at least one processor is configured to estimate the SpO2% by:
splitting the subset into alternating current (AC) and direct current (DC) components for the red data and the IR data; and
estimating the patient's SpO2% by the optical ratio expressed as:

$$R = \frac{AC_{rms\ RED} / DC_{rms\ RED}}{AC_{rms\ IR} / AC_{rms\ IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

11. The system of claim 8, wherein:
each peak of the series of peaks corresponds with a specific time of the time period; and
a specific peak of the series of peaks does not correspond with a heartbeat of the series of heartbeats if there is no heartbeat within the predetermined time window of the specific time corresponding with the specific peak.

12. The system of claim 7, wherein the system is configured to determine a predicted diagnosis of sleep apnea based on at least one of the red data, the IR data, and the series of heartbeats.

13. A system for deriving an estimated oxygen saturation percentage (SpO2%) for a patient comprising:
at least one processor communicably coupled to a patch for affixing to a patient and configured to:
receive reflectance red data and IR data derived from a photoplethysmography (PPG) sensor coupled to the patch, wherein:
the patch comprises a bottom surface located at a height from the PPG sensor of greater than 1 mm, upon attaching the bottom surface to the patient, the PPG sensor is pressed into the skin of the patient thereby increasing amplitude of the red data and IR data, and
the red data has a mean AC amplitude value of about 100 and the IR data has a mean AC amplitude value of about 300;
receive a series of heartbeats derived from a heartbeat detector;
compute a series of peaks of the red data and IR data for a time period;
compute a subset of the red data and IR data by excluding any peaks of the series of peaks that do not fall within a predetermined time window of a heartbeat of the series of heartbeats, wherein the series of heartbeats are associated with the time period;
estimate an oxygen saturation percentage (SpO2%) for the patient by computing an optical ratio of the red data and IR data included in the subset, thereby verifying peaks for the red data and IR data and eliminating potential noise and false peaks; and
display on a computer screen the estimated SpO2% for the patient.

14. The system of claim 13, wherein the heartbeat detector comprises an electrocardiogram (ECG) sensor, an accelerometer, bioimpedance sensor, and/or a beat detector.

15. The system of claim 14, wherein the heartbeat detector is coupled to the patch.

16. The system of claim 15, wherein the series of heartbeats are associated with the time period via a processor coupled to the patch.

17. The system of claim 16, wherein the red data, the IR data, and the series of heartbeats are associated with the time period via one or more clocks of the processor coupled to the patch.

18. The system of claim 13, wherein:
the PPG sensor is a first PPG sensor; and
the heartbeat detector is a second PPG sensor.

19. The system of claim 18, wherein the series of heartbeats are associated with the time period via synchronizing a second PPG sensor time period with the time period based on pulse transit time for the patient.

20. The system of claim 13, wherein:
the subset of the red data and the IR data comprises a particular peak of the series of peaks at a particular time;
the series of heartbeats includes a particular heartbeat occurring within the predetermined time window of the particular time; and
the estimated SpO2% for the patient is based on the particular peak.

21. The system of claim 13, wherein:
each peak of the series of peaks corresponds with a specific time of the time period; and a specific peak of the series of peaks does not correspond with a heartbeat of the series of heartbeats if there is no heartbeat within the predetermined time window of the specific time corresponding with the specific peak.

22. The system of claim 13, wherein the at least one processor is configured to estimate the SpO2% by:
splitting the subset into alternating current (AC) and direct current (DC) components for the red data and the IR data; and
estimating the patient's SpO2% by the optical ratio expressed as:

$$R = \frac{AC_{rms\ RED} / DC_{rms\ RED}}{AC_{rms\ IR} / AC_{rms\ IR}}$$

wherein R represents the optical ratio, ACrms RED represents the root means square of the red AC data of the subset, DCrms RED represents the root means square of the red DC data of the subset, ACrms IR represents the root means square of the IR AC data of the subset, and DCrms IR represents the root means square of the IR DC data of the subset.

23. The system of claim 13, wherein the system is configured to determine a predicted diagnosis of sleep apnea based on at least one of the red data, the IR data, and the series of heartbeats.

* * * * *